(12) United States Patent  
Jeong et al.

(10) Patent No.: US 7,999,089 B1  
(45) Date of Patent: Aug. 16, 2011

(54) RNA APTAMERS AND THE USES THEREOF

(75) Inventors: Sunjoo Jeong, Seoul (KR); Hee kyu Lee, Gunpo (KR); Min woo Park, Seoul (KR)

(73) Assignee: Industry-Academic Cooperation Foundation, Dankook University, Suji-gu, Yongin-si, Gyeonggi-do (KR)

( * ) Notice: Subject to any disclaimer, the term of this patent is extended or adjusted under 35 U.S.C. 154(b) by 358 days.

(21) Appl. No.: 12/064,384

(22) PCT Filed: Oct. 9, 2006

(86) PCT No.: PCT/KR2006/004048  
§ 371 (c)(1),  
(2), (4) Date: Feb. 21, 2008

(87) PCT Pub. No.: WO2007/043784  
PCT Pub. Date: Apr. 19, 2007

(30) Foreign Application Priority Data

Oct. 7, 2005 (KR) ........................ 10-2005-0094404

(51) Int. Cl.  
*C07H 21/04* (2006.01)  
*C12N 15/00* (2006.01)

(52) U.S. Cl. .................................. 536/23.1; 435/320.1
(58) Field of Classification Search .................. None  
See application file for complete search history.

(56) References Cited

U.S. PATENT DOCUMENTS

2006/0252045 A1* 11/2006 Chatterjee-Kishore et al. .. 435/6

OTHER PUBLICATIONS

Park, M.W. et al. : "Inhibition of the DNA binding by the TCF-1 binding RNA aptamer" Biochemical and biophysical research communications (Biochem. biophys. res. commun.) Biochemical and biophysical research communications, vol. 330, pp. 11-17 (Apr. 29, 2005).

Tuerk, C. et al.: Systematic evolution of ligands by exponential enrichment: RNA ligands to bacteriophage T4 DNA polymerase. Science, vol. 249(4968), pp. 505-510 (Aug. 3, 1990).

Famulok, M. et al. : "Intramers as promising new tools in functional proteomics." Chmistry & Biology, vol. 8 (10), pp. 931-939 (Oct. 2001).

Cassiday, L.A. et al. : "In Vivo Recognition of an RNA Aptamer by Its Transcription Factor Target" Biochemistry, vol. 40(8), pp. 2433-2438 (Feb. 27, 2001).

* cited by examiner

*Primary Examiner* — Richard Schnizer  
(74) *Attorney, Agent, or Firm* — Lexyoume IP Group, PLLC.

(57) ABSTRACT

The present invention relates to RNA aptamers and uses thereof, more precisely RNA aptamers interfering the interaction of TCF with other proteins by binding specifically to β-catenin, RNA aptamers binding specifically to HMG domains of TCF-I proteins and uses of the same. The RNA aptamer of the present invention can be effectively used for the development of an anticancer agent since it binds specifically to TCF-I to interrupt the interaction of TCF with β-catenin involved in tumorigenesis and metastasis and the transcriptional activity of TCF-I in relation to oncogenes.

7 Claims, 16 Drawing Sheets

5'-GGACGCGUGGUACC<u>AGGCCGAUCUAUGGACGCUAUAGGCACACCGGAUACUUUAACGAUUGGCU</u>AAGCUUCCGCGGGAUC-3'

Biotin-RNA Aptamer

W.B : Anti β-catenin Antibody

HCT 116

U6-Aptamer c-myc cyclin D1

18S RNA

Negative

U6-Aptamer    — 
U6-Vector    +    —    —

HCT116

U6-Vector

U6-NC

U6-Aptamer

TCF-1 FL

TCF-1 N100

TCF-1 C200

SEQUENCE LISTING

```
<160> NUMBER OF SEQ ID NOS: 24

<210> SEQ ID NO 1
<211> LENGTH: 50
<212> TYPE: RNA
<213> ORGANISM: Artificial Sequence
<220> FEATURE:
<223> OTHER INFORMATION: RNA Apamer

<400> SEQUENCE: 1
aggccgaucu auggacgcua uaggcacacc ggauacuuua acgauuggcu          50

<210> SEQ ID NO 2
<211> LENGTH: 50
<212> TYPE: DNA
<213> ORGANISM: Artificial Sequence
<220> FEATURE:
<223> OTHER INFORMATION: DNA Aptamer

<400> SEQUENCE: 2
aggccgatct atggacgcta taggcacacc ggatacttta acgattggct          50
```

<210> SEQ ID NO 3
<211> LENGTH: 26
<212> TYPE: DNA
<213> ORGANISM: Artificial Sequence
<220> FEATURE:
<223> OTHER INFORMATION: beta catenin primer

<400> SEQUENCE: 3
tgcggatccc acagatgctg aaacat                                        26

<210> SEQ ID NO 4
<211> LENGTH: 26
<212> TYPE: DNA
<213> ORGANISM: Artificial Sequence
<220> FEATURE:
<223> OTHER INFORMATION: beta catenin primer

<400> SEQUENCE: 4
gcgaattcag tctcattcca agccat                                        26

<210> SEQ ID NO 5
<211> LENGTH: 24
<212> TYPE: DNA
<213> ORGANISM: Artificial Sequence
<220> FEATURE:
<223> OTHER INFORMATION: U6-F1 primer

<400> SEQUENCE: 5
tgatgtcgac tagggacgcg tggt                                          24

<210> SEQ ID NO 6
<211> LENGTH: 18
<212> TYPE: DNA
<213> ORGANISM: Artificial Sequence
<220> FEATURE:
<223> OTHER INFORMATION: U6-R1 primer

<400> SEQUENCE: 6
gactctagag gatccccg                                                 18

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ctggccatga actacctgga                                               20

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
gtcacattga tcactctgg                                                19

<210> SEQ ID NO 9
<211> LENGTH: 25
<212> TYPE: DNA
<213> ORGANISM: Artificial Sequence
<220> FEATURE:
<223> OTHER INFORMATION: Primer

```
<400> SEQUENCE: 9
cgggatccac aagaaacggc tttca                                          25

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
gagaattcca ggtcagtatc aaacca                                         26

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
cttctgctgg aggccacagc aaacctcctc                                     30

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
ccaactccgg gatctggtca cgcaggg                                        27

<210> SEQ ID NO 13
<211> LENGTH: 70
<212> TYPE: DNA
<213> ORGANISM: Artificial Sequence
<220> FEATURE:
<223> OTHER INFORMATION: RNA aptamer #10

<400> SEQUENCE: 13
cggtgcgatc aagctgttta cattgcatgc taggacgacg cgcccgagcg ggtaccgatt    60
gtgtcgtcgg                                                           70

<210> SEQ ID NO 14
<211> LENGTH: 69
<212> TYPE: DNA
<213> ORGANISM: Artificial Sequence
<220> FEATURE:
<223> OTHER INFORMATION: RNA aptamer #9

<400> SEQUENCE: 14
tgctgacaat tctcgtgcct ctccatggtc tgcggctgag aaggttcgcc aagttgtggg    60
ccggggtgc                                                            69

<210> SEQ ID NO 15
<211> LENGTH: 67
<212> TYPE: DNA
<213> ORGANISM: Artificial Sequence
<220> FEATURE:
<223> OTHER INFORMATION: RNA aptamer #20

<400> SEQUENCE: 15
ttcccgcggt ggaaagcgtt gggtagcggc tccgatggag agtggtgcgc cttgcctgct    60
``` ggccttg                                                              67

<210> SEQ ID NO 16
<211> LENGTH: 29
<212> TYPE: DNA
<213> ORGANISM: Artificial Sequence
<220> FEATURE:
<223> OTHER INFORMATION: TCF-1 N100 primer

<400> SEQUENCE: 16
tttgaattct tgattctggc gggggcggc                                      29

<210> SEQ ID NO 17
<211> LENGTH: 28
<212> TYPE: DNA
<213> ORGANISM: Artificial Sequence
<220> FEATURE:
<223> OTHER INFORMATION: TCF-1 N100 primer

<400> SEQUENCE: 17
acagaagctt gaagtttgtc cgggaaag                                       28

<210> SEQ ID NO 18
<211> LENGTH: 27
<212> TYPE: DNA
<213> ORGANISM: Artificial Sequence
<220> FEATURE:
<223> OTHER INFORMATION: full primer

<400> SEQUENCE: 18
atatgtcgac catgtcatcg gaaggaa                                        27

<210> SEQ ID NO 19
<211> LENGTH: 26
<212> TYPE: DNA
<213> ORGANISM: Artificial Sequence
<220> FEATURE:
<223> OTHER INFORMATION: C200 primer

<400> SEQUENCE: 19
ttgaattcca caggccgctg cagacc                                         26

<210> SEQ ID NO 20
<211> LENGTH: 31
<212> TYPE: DNA
<213> ORGANISM: Artificial Sequence
<220> FEATURE:
<223> OTHER INFORMATION: c200 primer

<400> SEQUENCE: 20
atatgtcgac gagcactgtc atcggaagga a                                   31

<210> SEQ ID NO 21
<211> LENGTH: 15
<212> TYPE: DNA
<213> ORGANISM: Artificial Sequence
<220> FEATURE:
<223> OTHER INFORMATION: TRE

<400> SEQUENCE: 21
ggtaagatca aaggg                                                     15

<210> SEQ ID NO 22
<211> LENGTH: 20
<212> TYPE: DNA
<213> ORGANISM: Artificial Sequence

```
<220> FEATURE:
<223> OTHER INFORMATION: GAPDH-F

<400> SEQUENCE: 22
tgacatcaag aaggtggtga                                                      20

<210> SEQ ID NO 23
<211> LENGTH: 20
<212> TYPE: DNA
<213> ORGANISM: Artificial Sequence
<220> FEATURE:
<223> OTHER INFORMATION: GAPDH-R

<400> SEQUENCE: 23
tccaccaccc tgttgctgta                                                      20

<210> SEQ ID NO 24
<211> LENGTH: 81
<212> TYPE: RNA
<213> ORGANISM: Artificial Sequence
<220> FEATURE:
<223> OTHER INFORMATION: selected RNA aptamer

<400> SEQUENCE: 24
ggacgcgugg uaccaggccg aucuauggac gcuauaggca caccggauac uuuaacgauu          60
ggcuaagcuu ccgcggggau c                                                    81
```

RNA APTAMERS AND THE USES THEREOF

TECHNICAL FIELD

The present invention relates to RNA aptamers and the uses thereof, more precisely, RNA aptamers inhibiting interaction between TCF and β-catenin by binding specifically to β-catenin, RNA aptamers binding specifically HMG domain of TCF-1, and the uses thereof.

BACKGROUND ART

β-catenin is a multifunctional protein that plays critical roles in cell adhesion as well as signaling (Moon R T et al., Nat Rev Genet. 5(9):691-701, 2004; Nelson W J and Nusse R. Science. 303(5663):1483-7, 2004). It was first identified as a component of a cell adhesion complex that links transmembrane cadherin proteins and cytoskeleton. It is also a central component of the developmentally important Wnt pathway regulating cell growth and differentiation during embryonic development and tumorigenesis (Gregorieff A and Clevers H. Genes Dev. 19(8):877-890, 2005). In the absence of Wnt, most of the β-catenin in epithelial cells is attached to the plasma membrane, where it is associates with E-cadherin in adherens junctions. Cytosolic β-catenin is located in a multiprotein complex consisting of the adenomatous polyposis coli (APC) protein, axin/conductin, and glycogen synthase kinase-3β (GSK-3β). However, mutations of APC or β-catenin are frequently found in various types of cancer cells (Polakis P. Genes Dev. 14(15):1837-1851, 2000). Mutations in one of the ser/thr-phosphorylation sites of β-catenin stabilize it and lead to transcription of target genes, such as cyclin D1 and c-myc, independent of external Wnt signals (Morin P J et al., Science. 275(5307):1787-1790, 1997; Rubinfeld B et al., Science. 275(5307):1790-1792, 1997; Tetsu 0 and McCormick F. Nature. 398(6726):422-426, 1999; He et al., Science. 281(5382):1509-1512, 1998). TCF proteins bind to the enhancers of these target genes through their HMG-1 (High Mobility Group-1) DNA binding domains and provide the binding site for β-catenin (Behrens J et al., Nature. 382 (6592):638-642, 1996; Morin P J et al., Science, 275(5307): 1787-1790, 1997).

Since Wnt signaling is critical for tumor development, the interference of β-catenin-mediated signaling has been proposed as a therapeutic strategy, especially in cancers (Lustig B and Behrens J. J Cancer Res Clin Oncol. 129(4):199-221, 2003; Lee et al., Biochem Biophys Res Commun. 327(1): 294-299, 2005). Molecules that could modulate this process would be useful for anti-tumor therapy (Tolwinski & Wieschaus, PLoS Biol. 2(4):486-493, 2004; Lipinski et al., Mol. Ther. 10(1):150-61, 2004). A couple of chemical agents have been reported to disrupt the β-catenin/TCF association in cancer cells (Nath et al., Proc Natl Acad Sci USA. 100(22): 12584-9, 2003; Lepourcelet et al., Cancer Cell. 5(1):91-102, 2004). However, since β-catenin is a component of several different protein complexes, more specific tools are needed to selectively disrupt the β-catenin interaction with TCF without affecting the interaction with E-cadherin.

T-cell factor-1 (TCF-1) was originally identified as a T-cell specific transcription factor that bound to specific DNA through its high mobility group-1 (HMG-1) DNA binding domain (M van de Wetering et al., EMBO J. 10: 123-32, 1991; M. Oosterwegel et al., J. Exp. Med. 173: 1133-1142, 1991; H. C. Clevers et al., Immunol. Today 14: 592-597, 1993). Even though transgenic and knockout approaches suggested that TCF-1 was likely to be involved in the expansion of T-lymphocytes, exact functions of the TCF-1 protein in T-cell development need to be understood (M. Oosterwegel et al., Development 118: 439-448; S. Verbeek et al., Nature 374: 70-74, 1990; R. M. Okamura et al., Immunity 8: 11-20, 1998).

TCF family proteins bind to DNA in a sequence-specific manner and they seem to act as architectural proteins for the assembly of other transcription factors (J. J. Love et al., Nature 376: 791-795, 1995). Identification of β-catenin as a potent transcriptional co-activator of TCF family proteins led to a greater understanding of their function (H. Clevers and M. van de wertering, Trends Genet. 13: 485-489, 1997; J. Behrens et al., Nature 382: 638-642, 1996). Since it is highly expressed in various cancer cells, it seemed possible that the formation of a transcriptional complex by an oncogenic β-catenin with TCF might be a central event in cancer cell development (V. Korniek et al., Science 275: 1784-1787, 1997; P. J. Morin et al., Science 275: 1787-1790, 1997; B. Rubinfeld et al., Science 275: 1790-1792, 1997).

The TCF/β-catenin protein complex is also a critical regulator of early developmental events such as axis formation in the *Xenopus* embryo and Wingless signaling in *Drosophila* (M. Molenaar et al., Cell 86: 391-399, 1996; M. van de Wetering et al., Cell 88: 789-799, 1997; E. Brunner et al., Nature 385: 829-833, 1997). In addition, it was recently shown that the TCF/β-cadenin complex mediating Wnt signaling seems to be an important pathway in immature thymocyte development (V. Ionnidis et al., Nat. Immunol. 2: 691-697, 2001). These findings began to point to the role of TCF family proteins as critical modulators of the expression of genes that control the decision between proliferation and apoptosis (J. Roose and H. Clevers, Biochem. Biophys. Acta 87456: M23-M37: 1999; J. Roose et al., Nature 395: 608-612, 1998). For example, TCF/β-catenin transcribes genes implicated in cancer development, such as cyclin D1 and c-myc (O. Tetsu and F. McCormick, Nature 395: 608-612, 1998; T. C. He et al., Science 281: 1509-1512, 1998).

Aptamers, which are short single-stranded oligonucleotides, form a three-dimensional structure enabling binding to targets owing to their high affinity and specificity. These aptamers not only specifically bind to target proteins but also successfully disrupt their functions, suggesting that they are very useful for understanding the functions of the target proteins.

Reiterated in vitro selection procedures are able to select specific RNA molecules from random RNA library, and nucleic acids selected by this procedure are generally referred to as aptamers (A. D. Ellington and J. W. Szostak, Nature 346: 818-822, 1990; C. Tuerk and L. Gold, Science 249: 505-510, 1990). Because of the large size ($10^{14}$-$10^{15}$) of RNA libraries and the ease of generating RNA molecules by in vitro enzymatic reactions, RNA libraries are superior to other biological or synthetic libraries for selecting high affinity aptamers (E. N. Brody and L. Gold, Rev. Mol. Biotechnol. 74: 5-13, 2000).

Interest in potential uses of RNA aptamers as therapeutics has been increased (Nimjee et al., Trends Cardiovasc Med. 15(1):41-45, 2005). High affinity RNA aptamers can be selected by the SELEX (Systematic Evolution of Ligands by Exponential Enrichment) procedure (Ellington et al., Nature 346(6287):818-822, 1990; Brody & Gold, J Biotechnol. 74(1):5-13, 2000). RNA aptamers have an advantage over small chemicals as inhibitors because they usually provide extensive binding surface to target proteins. Pathogenic protein-protein interaction might be a great target for RNA aptamers, because high affinity RNA binds to target protein and interferes its binding to other proteins in the complex. Moreover, RNA aptamer can be expressed in the cells as an intramer using RNA expression vector system (Famulok & Mayer, Chembiochem. 6(1):19-26, 2005).

Descriptions on aptamers can be found in following patents. For example, Korean Patent No. 10-2003-0054412 describes a pharmaceutical agent containing a RNA aptamer for the acceleration of coagulation. Korean Patent No. 10-2002-7009983 describes an aptamer containing a reporter gene which is involved in signaling of homologous ligands in the solution. International Patent WO 2003/027319 describes an aptamer containing two or more nucleobase-containing sequences linked by Watson-Crick or homologous binding. However, any of those descriptions describes on the aptamer interacting with TCF binding site of β-catenin or interacting with DNA binding domain of TCF-1.

Therefore, the present inventors selected β-catenin binding RNA aptamers and stably expressed these aptamers as cell-line specific RNA intramers. The present inventors also confirmed that the expressed RNA intramers could inhibit transcription activity of β-catenin and expression of a target gene. Then, the present inventors further completed this invention by confirming that the in vitro selected TCF-1 binding RNA aptamer (RNA aptamer #10) binds to TCF-1 protein to disrupt the binding with cancer-related genes to disrupt the transcription, so that it can be effectively used for the development of an anticancer agent.

Disclosure

Technical Problem

It is an object of the present invention to provide a β-catenin binding RNA aptamer, a RNA aptamer binding specifically HMG domain of TCF-1, and a use thereof.

Technical Solution

To achieve the above object, the present invention provides a β-catenin binding RNA aptamer.

The present invention also provides a gene expression regulator containing the RNA aptamer.

The present invention further provides an inhibitor of the interaction between β-catenin and other proteins.

The present invention also provides an anticancer agent containing the RNA aptamer.

The present invention also provides an RNA aptamer binding specifically HMG domain of TCF-1.

The present invention also provides an inhibitor of the interaction between TCF-1 and another gene, which contains the RNA aptamer.

The present invention also provides a gene expression regulator containing the RNA aptamer.

The present invention also provides an anticancer agent containing the RNA aptamer.

Hereinafter, the present invention is described in detail.

The present invention provides a β-catenin binding RNA aptamer.

RNA aptamer is a short single-stranded oligonucleotide forming a three-dimensional structure that is able to bind to a target with high affinity and specificity. To generate RNA aptamers that bind to β-catenin, the present inventors used armadillo repeats (Arm 1-12) of this protein as the target for in vitro selection because they contain an interaction motif for TCF-4 protein (see FIG. 1). 50 random RNA sequences ($1 \times 10^{15}$ molecules) were used as starting materials (Kim & Jeong, Biochem. Biophys. Res. Commun 320:1181-1186, 2004) for SELEX (Systematic Evolution of Ligands by Exponential enrichment) and only RNAs bound to recombinant armadillo repeats were selected. The binding of the selected RNA to (β-catenin was investigated in vitro. As a result, RNA-EMSA bound to full-length β-catenin (see FIG. 4) but not to any other proteins. The above result indicates that RNA aptamer of the invention specifically binds to (β-catenin.

The present invention also provides a gene expression regulator containing the RNA aptamer.

β-catenin is involved in cytoplasmic cell adhesion and regulates the expression of a target gene in the nucleus. The present inventors selected a high affinity RNA aptamer for β-catenin and expressed it as an intramer by using RNA expression vector in order to observe specific binding to β-catenin of a target cell not in a cytoplasmic cell adhesion complex but in a transcription complex in the nucleus (RNA intramer indicates the intracellular expressed RNA aptamer). A nucleus specific RNA expression vector system can be any vector that is able to express the inserted sequence in the nucleus, and is preferably the pTZU6+27 vector under the control of RNA polymerase III.

The present inventors performed luciferase assay with colon cancer cell lines expressing β-catenin at high level, and confirmed the inhibition of RNA intramer dose-dependent β-catenin dependent TCF transcription activity (see FIG. 10). It has been known that β-catenin binds to TCF protein family and activates the transcription of cyclin D1 and c-myc promoter (Tetsu & McCormick, 1999; He et al., 1998). Based on that, the present inventors tested if RNA intramer could inhibit the transcription of cyclin D1, the target gene of β-catenin. As a result, cyclin D1 mRNA expression was reduced and the similar result was observed with c-myc expression (see FIG. 11).

As explained hereinbefore, the present inventors selected RNA aptamer specifically binding to β-catenin in vitro and stably expressed it as RNA intramer in the nucleus of a target cell line, and thereby confirmed that RNA intramer inhibited transcription activity of β-catenin and reduced the expression of a target gene but did not affect cell adhesion.

The present invention further provides an inhibitor of the interaction between β-catenin and other proteins.

The RNA aptamer of the invention also inhibits the interaction between β-catenin and TCF protein and the formation of intra-nucleus protein complexes (FIG. 13 and FIG. 14), so that it can be used as a pathologic protein-protein interaction inhibitor.

The present invention also provides an anticancer agent containing the RNA aptamer.

Since the RNA intramer reduced the expression of cyclin D1, the present inventors assumed that the RNA was effective in arresting the cell line in G1/S transition of cell cycle and to confirm the notion the inventors performed the flow cytometric analysis. As a result, a significant proportion of the cell line was effectively arrested in G1 stage (see FIG. 17).

To test whether this cell line had reduced tumor forming potential, the present inventors assayed soft agar colony formation. No colonies were formed by the RNA intramer stable cell line, whereas a large number of colonies were formed in control stable cell line. These results indicate that the β-catenin binding RNA intramer is effective in arresting cell adhesion and ultimately reducing tumorigenesis (see FIG. 18).

The present invention also provides a RNA aptamer binding specifically HMG domain of TCF-1.

The present inventors previously selected RNA aptamers binding to HMG domain of TCF-protein in vitro. In this invention, the inventors examined if the selected RNA aptamer could actually bind to TCF-1 proteins. As a result, RNA aptamer #10 bound to DNA binding site containing HMG domain (C200, C), but not to β-catenin binding domain (N100, N) of N-terminal. The RNA aptamer #10 did not bind to other DNA binding domains of other proteins such as β-catenin or NFAT (NF).

The present inventors performed competition experiment to examine the binding specificity of RNA aptamer #10 for TCF-1 protein. A gradual decrease in the strength of the bound band of TCF-1 binding RNA aptamer #10 was observed as the amount of RNA #10 increased. However, non-binding RNA #9 or original RNA pool (Ori) did not compete for binding of RNA aptamer #10 (see FIG. 20 and FIG. 21), suggesting that RNA aptamer #10 has binding specificity to TCF-1 protein.

The present invention also provides an inhibitor of the interaction between TCF-1 and another gene, which contains the RNA aptamer.

In the present invention, DNA oligonucleotide (TRE, TCF responsive element) containing TCF-1 binding sequence was reacted with TCF-1, RNA aptamer #10 and tRNA. The binding of TRE to TCF-1 protein was disrupted by the increase of the amount of RNA aptamer #10 but not by non-specific tRNA (see FIG. 23).

Therefore, it has been confirmed that RNA aptamer #10 inhibits TCF-1 specific DNA binding.

The present invention also provides a gene expression regulator containing the RNA aptamer.

As a DNA binding transcription factor, TCF protein binds strongly to other transcription activation factors to activate various target genes. The RNA aptamer of the invention strongly binds to HMG domain of TCF-1 protein to inhibit the interaction with other transcription factors, which means the RNA aptamer of the invention can be used to regulate the expressions of TCF-1 binding target genes such as cyclin D1, c-myc, etc.

The present invention also provides an anticancer agent containing the RNA aptamer.

Cyclin D1 and c-myc are known to be involved in tumorigenesis. Since a RNA aptamer is able to interferer the binding of TCF-1 with other transcription activation factors by specifically binding itself to the transcription factor TCF-1, the RNA aptamer can be effectively used as a therapeutic agent for cancer caused by the expression and activation of a target gene. The failure in binding of β-catenin to TCF-1 results in the development of various cancers, in particular colon cancer and rectal cancer are more frequently developed. Thus, the anticancer agent containing the RNA aptamer of the invention can be effectively used for the treatment of colon cancer and rectal cancer. (Lustig B and Behrens J. J, Cancer Res Clin Oncol. 129(4): 199-221, 2003; Gregorieff A & Clavers H. Genes Dev. 19(8): 87-90, 2005).

The anticancer agent containing the RNA aptamer of the present invention can additionally include one or more effective ingredients having the same or similar functions to the RNA aptamer of the invention. Pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (the newest edition), Mack Publishing Company, Easton Pa.

The anticancer agent containing the RNA aptamer of the present invention can be administered parenterally (for example, intravenous, hypodermic, local or peritoneal injection). The effective dosage of the anticancer agent can be determined according to weight, age, gender, health condition, diet, administration frequency, administration method, excretion and severity of a disease. The anticancer agent of the invention preferably contains the RNA aptamer by 10~95 weight % and more preferably 25~75 weight %. The administration frequency is preferably once to several times a day. The effective intracellular content of the RNA aptamer is approximately 1 nM~1000 nM and more preferably 100 nM~500 nM. However, the dosage of the aptamer could be under or more than the above range.

DESCRIPTION OF DRAWINGS

The application of the preferred embodiments of the present invention is best understood with reference to the accompanying drawings, wherein:

FIG. 1 is a schematic diagram illustrating various β-catenin proteins used in the examples of the invention, and specifically 12 armadillo (Arm) repeats and TCF-1 binding sites are shown,
FIG. 2 is a photograph illustrating the results of GST-pull-down assay after selection cycles (cycle 0, cycle 6 and cycle 8),
FIG. 3 illustrates the sequence of the selected RNA aptamer having the sequence of SEQ ID NO:24,
FIG. 4 is a photograph illustrating the result of RNA-EMSA of the selected RNA aptamer binding to GST 3-catenin protein,
FIG. 5 is a photograph illustrating the results of Northern blotting of the cells transfected with U6-aptamer,
FIG. 6 is a photograph illustrating the stabilization of U6-RNA intramer,
FIG. 7 is a photograph illustrating the results of RNA co-immunoprecipitation assay with the cell lines transfected with U6-NC (nucleocapsid), U6-aptamer (U6-Apt) or U6 (vector),
FIG. 8 is a photograph illustrating the stabilization of endogenous β-catenin upon LiCl treatment in 293T cells transfected with the RNA aptamer expression vector,
FIG. 9 is a photograph illustrating the results of luciferase assay of 293T cells transfected with TCF-1 binding (OT) luciferase reporter together with U6 vector or U6-RNA aptamer,
FIG. 10 is a graph illustrating the results of luciferase assay of HCT116 cells co-transfected with TCF-responsive (OT) or mutant (OF) luciferase reporter together with U6 vector (−), RNA aptamer for nucleocapsid in U6 vector (U6-NC) or U6-aptamer,
FIG. 11 is a graph illustrating the results of luciferase assay of HCT116 cells co-transfected with −1745 cyclin D1 promoter luciferase reporters (WT, wild-type; MT, mutant TCF sites) together with U6 vector, U6-NC or U6-aptamer,
FIG. 12 is a photograph illustrating the results of RT-PCR analysis of various RNAs (c-myc, cyclin D1 and GAPDH mRNA) in mock, U6 vector, and U6-Aptamer expressing HCT116 cells,
FIG. 13 is a photograph illustrating the results of Western blot analysis with anti-TCF and anti-β-catenin antibody. TCF and β-catenin were incubated and immunoprecipitated in the presence (+) or absence (−) of RNA aptamer, followed by Western blot analysis,
FIG. 14 is a photograph illustrating the results of co-immunoprecipitation of HCT116 cells over-expressing U6 vector or U6-aptamer using anti-β-catenin antibody,
FIG. 15 is a photograph illustrating the results of RT-PCR of HCT116 cell lines. Stable U6-NC, U6-aptamer (clone #6) and U6 vector cell lines were tested and stable expression of RNA intramer was confirmed therein,
FIG. 16 is a photograph illustrating the results of Western blot analysis of HCT116 cell lines transfected with U6-RNA intramer,
FIG. 17 is a set of graphs illustrating the results of the flow cytometric analysis of the RNA intramer expressing stable cell lines,
FIG. 18 is a set of photographs illustrating the results of soft agar colony forming assay of the RNA intramer expressing stable cell lines,
FIG. 19 is a schematic diagram of recombinant GST-TCF-1 protein used in the present invention,
FIG. 20 is a photograph illustrating the results of GST pull-down assay of radiolabeled RNA aptamer #10, G: GST protein, F: full-length TCF-1 protein, C: TCF-1 C200, N: TCF-1 N100, β: β-catenin, NF: NFAT protein
FIG. 21 is a photograph illustrating the results of RNA-EMSA with labeled RNA aptamer #10 and TCF-1 C200 protein on its own in the presence of excess unlabeled RNA aptamer #10, RNA #9 and RNA #20 as competitors,
FIG. 22 is a photograph illustrating the results of RNA-EMSA with radio-labeled RNA aptamer #10 and TCF-1 protein of an intracellular nucleus extract in the presence of excess unlabeled RNA aptamer #10, RNA #9 and RNA (Ori) as competitors, Lane 1: no nuclear extract (TCF-1)
Lane 2: vector transfected cells (GST-TCF-1)
Lane 3: TCF-1 cDNA transfected cells
FIG. 23 is a photograph illustrating the inhibition of the binding of TRE (TCF-1 response element) to TCF-1 C200 by RNA aptamer #10, Lane 1: labeled DNA only
Lane 2: binding in the presence of TCF-1 C200 protein
Lanes 3-6: with addition of 2, 20, 200 and 1000 nM of unlabeled RNA aptamer #10
Lanes 7-9: with 20, 200 and 1000 nM of unlabeled tRNA
FIG. 24 is a photograph illustrating the inhibition of the binding of TRE to TCF-1 full length protein by RNA aptamer #10.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

β-Catenin Binding Aptamer

Example 1

Plasmids and Reagents pCAN-β-catenin was kindly provided by Dr. McCrea (University of Texas M.D. Anderson Cancer Center), pTZU6+26 was a gift of Dr. David Engelke (University of Michigan), and the luciferase reporter plasmids, pGL3-OT (an improved version of TOPFLASH) and pGL3-OF (mutant), were from Drs. Shivadasani and Vogelstein (Johns Hopkins University). The wild-type and three TCF sites mutant −1745 cyclin D1 promoter reporters were kindly donated by Dr. Pestell (Albert Einstein College of Medicine). The control vector, *Renilla* luciferase pRL-TK for normalizing transfection frequencies was provided with the dual luciferase kit (Promega) and pCMV-β was from Clonetech. Anti-β-catenin polyclonal (C-18), anti-TCF-4 polyclonal (H-125) and anti-cyclin D1 monoclonal (HD11) antibodies were from Santa Cruz, and the anti-γ-catenin and E-cadherin monoclonal antibodies were purchased from Transduction Laboratories.

Example 2

In Vitro RNA Binding Assay

<2-1> Cloning and Expression of GST-β-Catenin Proteins

Bacterial expression vectors for recombinant β-catenin proteins were obtained by PCR amplification of the pCAN-β-catenin plasmid. GST-Arm 1-12 (amino acids 129-695) was amplified with primers containing BamHI (SEQ. ID. No: 3) and EcoRI (SEQ. ID. No: 4) restriction sites. For the PCR, a reaction mixture having the total volume of 100 μl was prepared by mixing DNA (10 μM), 10×Mg$^{2+}$ free buffer, 2.5 mM MgCl$_2$, 250 nM 5' Primer, 250 nM 3' Primer and 100 μM Taq polymerase 1u (Takara). Then, PCR was performed as follows; predenaturation at 95° C. for 5 minutes, denaturation at 95° C. for 1 minute, annealing at 55° C. for 1 minute, polymerization at 72° C. for 1 minute, 30 cycles from denaturation to polymerization, and final extension at 72° C. for 10 minutes. The PCR products were cloned into pBluesript II-SK vector using these restriction sites. The inserts were cut out with BamHI and XhoI and ligated to pGEX-5X-1 vector (Amersham Biosciences) to produce the GST-β-catenin fusion vector. Recombinant GST-fusion proteins were expressed in *E. coli* and purified as described previously (Lee et al. Biochem. Biophys. Res. Commun. 327: 294-299, 2005).

<2-2> In Vitro RNA Selection and RNA Binding Assay

<2-2-1> Aptamer Selection and Identification

Figure 1:
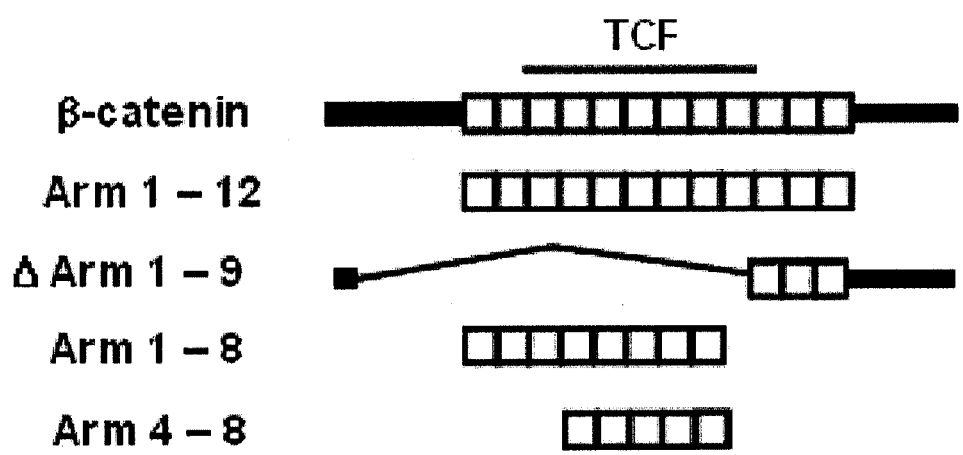
FIG. 1~FIG. 4 illustrate the affinity and binding specificity of RNA aptamer to β-catenin protein.

In order to generate RNA aptamers that bind to β-catenin, the present inventors used armadillo repeats 1-12 (Arm 1-12) of this protein as the target for in vitro selection because they contain an interaction motif for TCF-4 (FIG. 1A).

Figure 2:
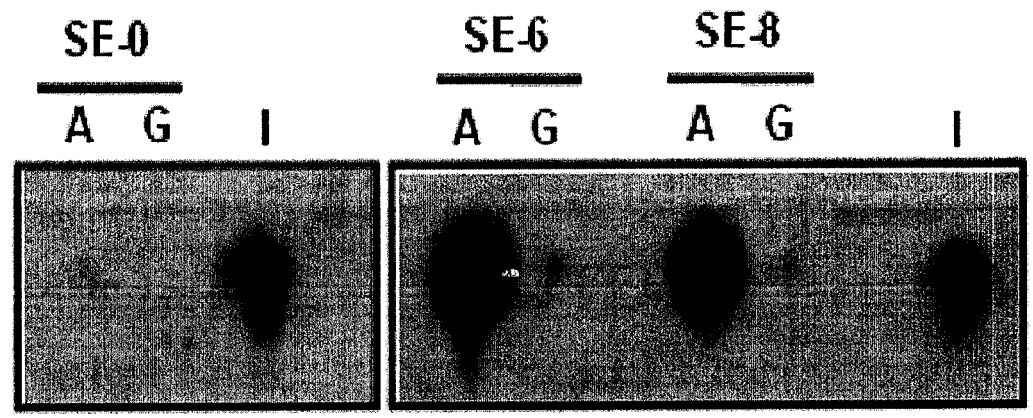
Figures 3, 4:
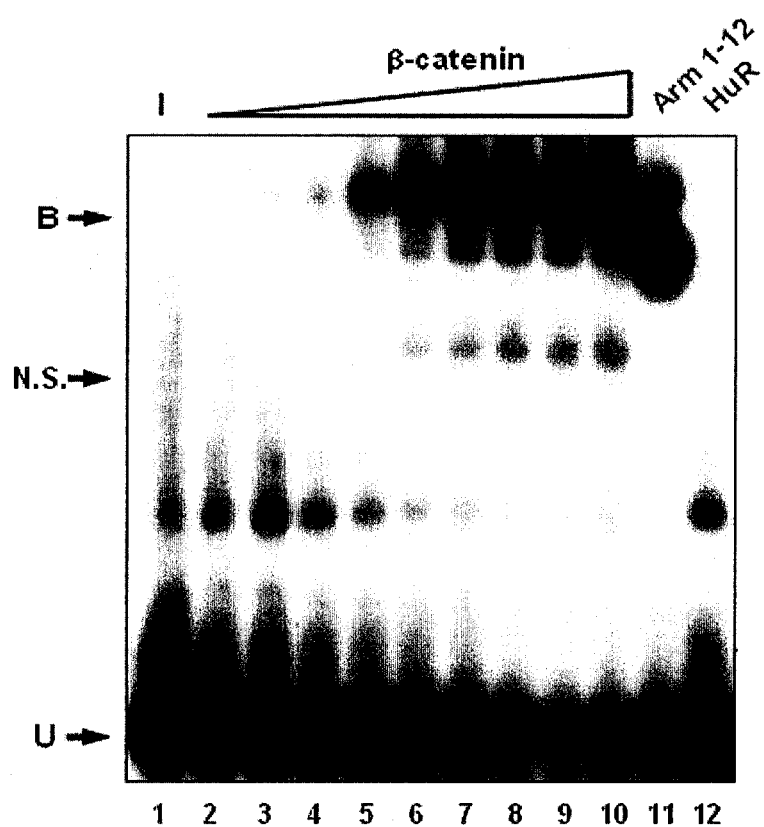

RNA aptamers were selected by using SELEX (Systematic Evolution of Ligands by Exponential enrichment) procedure. Particularly, an RNA library of random 50-nucleotide sequences (1×10$^{15}$ molecules) was used as starting material for SELEX. GST-bound RNA was discarded and RNA bound to the GST armadillo repeat was selected with Glutathione-Sepharose 4B beads. The selected RNA was amplified and the library that was newly constructed using the amplified aptamers was used as a starting material. After 8 cycles of selection, RNA aptamers were separated. The selected RNA bound to the protein after 6 cycles of selection (selection 6, SE6, FIG. 2). A similar level of binding was observed after 8 cycles of selection (SE8). Individual RNA molecules were isolated from the SE8 RNA pools, and 40 independent clones were sequenced. As a result, all clones were confirmed to have the same sequence (Kim & Jeong, Biochem. Biophys. Res. Commun 320:1181-1186, 2004; Lee S K et al., Biochem Biophys Res Commun. 327:294-299, 2005) (FIG. 3).

<2-2-2> In Vitro RNA Binding Assay

After 8 cycles of SELEX selection, the selected sequences were digested with EcoRI and BamHI, followed by cloning into pUC19 to prepare pUC19-aptamer. To test for RNA binding, the RNA was radiolabeled as described previously (Kim & Jeong, Biochem. Biophys. Res. Commun 320:1181-1186, 2004), incubated with GST-β catenin and assayed by GST pull-down (Kim & Jeong, Biochem. Biophys. Res. Commun 320:1181-1186, 2004) or RNA-EMSA (RNA-Electrophoretic Mobility-Shift Assay) (Kim & Jeong, Biochem. Biophys. Res. Commun 320:1181-1186, 2004). The RNA aptamer had binding affinity for the full length β-catenin, which was 5 nM (FIG. 4). However, the RNA aptamer did not bind to other proteins, such as RNA binding HuR, β-catenin interacting TCF1 or the unrelated GST protein. Thus, the RNA aptamer of the present invention was proved to specifically bind to β-catenin.

Example 3

Expression of RNA Aptamer and Specific Association with Cellular β-Catenin

Since the RNA aptamer exhibited high affinity and specificity for β-catenin in vitro, the present inventors tested its effect in the mammalian cells.

<3-1> Construction and Expression of Intramer

The present inventors placed the RNA aptamer sequence under the control of U6 promoter of pTZU6+27 that generates small RNA intramer transcripts restricted to the nucleus, resulting in the construction of the expression vector pU6-aptamer (Paul C P et al., Nature Biotechnol 20: 505-50, 2002).

Figure 5:
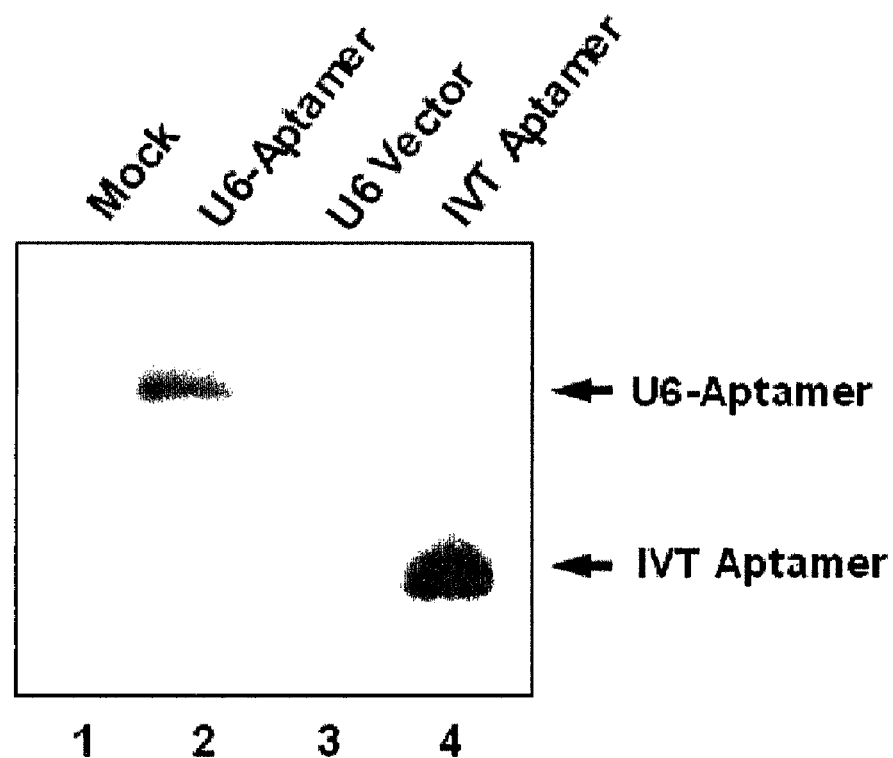
FIG. 5~FIG. 7 illustrate the expression and stabilization of U6-RNA intramer.
Figure 6:
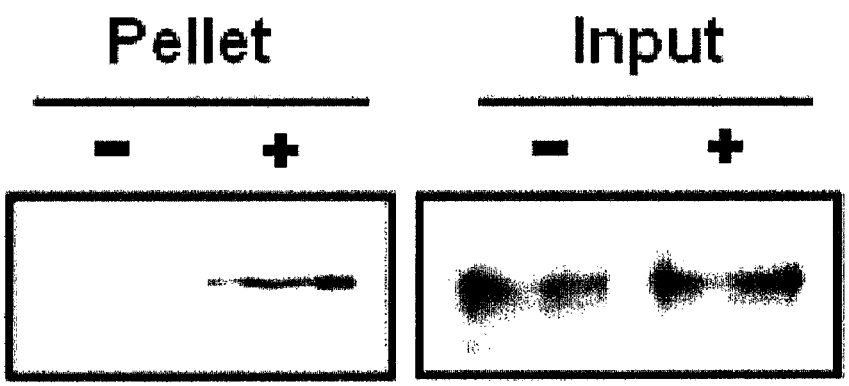

To clone the aptamer sequence into pTZU6+27, the DNA was amplified from the pUC19-aptamer with primers U6-F1 (SEQ. ID. NO: 5) and U6—R1 (SEQ. ID. NO: NO. 6). After denaturation at 94° C. for 5 minutes, a reaction mixture having the total volume of 100 a was prepared by mixing DNA (10 μM), 10×Mg$^{2+}$ free buffer, 2.5 mM MgCl$_2$, 250 nM 5'Primer, 250 nM 3' Primer and 100 μM Taq polymerase 1u (Takara). Then, PCR was performed as follows; predenaturation at 95° C. for 5 minutes, denaturation at 95° C. for 1 minute, annealing at 55° C. for 1 minute, polymerization at 72° C. for 1 minute, 30 cycles from denaturation to polymerization, and final extension at 72° C. for 10 minutes. The PCR product was digested with Sal I and XbaI and cloned into the same sites of the pTZU6+27 vector, resulting in the construction of pU6-aptamer. Plasmid U6-NC (nucleocapsid) (Kim & Jeong, Biochem. Biophys. Res. Commun 320:1181-1186, 2004) was used as a negative control in all experiments. Construction of pDHFR-aptamer was similar to the one described previously (Kim & Jeong, Biochem. Biophys. Res. Commun 320:1181-1186, 2004). High expression level of the RNA intramer was confirmed by Northern blotting (FIG. 5) and real-time RT-PCR analysis of 293T cells transfected with the U6-aptamer. The present inventors also confirmed the stable expression of the RNA intramer for 5 days after transfection.

<3-2> Cell Culture, Transfection and Luciferase Assay

Human embryonic kidney 293T cells, human colorectal carcinoma HCT116 cells and adenocarcinoma SW480 cells (American Type Culture Collection) were cultured in DMEM with 10% FBS. HCT116 cells and SW480 cells were transfected with pU6-aptamer prepared in Example <3-1> using lipofectAMINE (Invitrogen). For luciferase assays, the cells were co-transfected with the luciferase reporter, pU6-aptamer and pCMV-β-catenin. Luciferase activity was determined with a Luciferase assay system (Promega) together with a Turner Luminometer TD-20/20.

<3-3> Binding Between RNA Intramer and β-Catenin

The present inventors performed the following experiments to investigate the binding between the RNA aptamer and β-catenin.

<3-3-1> RNA Co-Immunoprecipitation Assays

HCT116 cells were transfected with RNA expression vector, U6-apatmer, or control vector, pU6-NC. Nuclear extracts were pre-cleared with protein-G-Sepharose beads, and immunoprecipitated with normal rabbit IgG, anti-γ-catenin antibody, or anti-β-catenin antibody at 4° C. for overnight. Pellets and supernatants were subsequently extracted with phenol to purify bound RNA, which was reverse transcribed and PCR amplified with specific primers for the aptamer (SEQ. ID. NO: 5 and NO: 6) or for GAPDH (SEQ. ID. NO: 22 and NO: 23).

<3-3-2> Biotin RNA Pull-Down Assay

The RNA aptamer was transcribed in vitro in the presence of 4-thio UTP (USB) and end-labeled with Biotin (Pierce). For RNA pull-down assay, 4.4 μg of labeled aptamer was incubated with 20 μg of SW480 nuclear extract for 30 minutes at room temperature, and irradiated with UV for 15 minutes. Complexes were isolated with streptavidin-conjugated Dynabeads (New. England BioLabs) and proteins on the beads and in the supernatant were analyzed by Western blotting.

Figure 7:
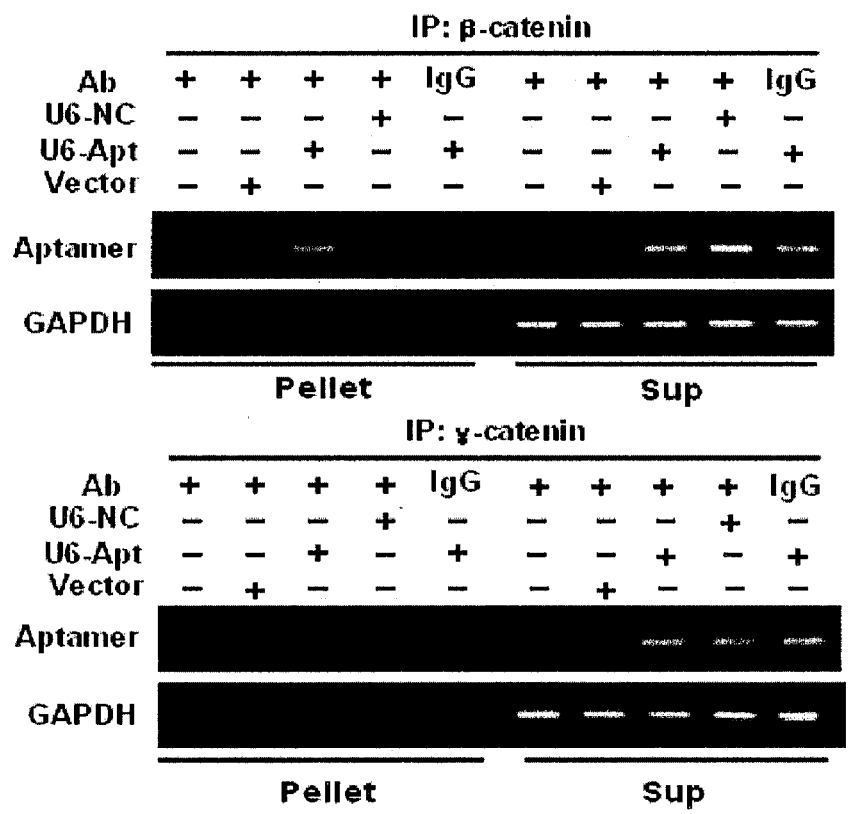

As a result, the present inventors detected β-catenin in the biotin-RNA precipitated lane, but not in control lane. When β-catenin was immunoprecipitated with antibody, only the U6-RNA intramer was co-immunoprecipitated, not a control RNA intramer to NC protein (nucleocapsid of HIV-1) or vector RNA (FIG. 7).

To test the specificity of the intracellular protein binding, the present inventors performed the same experiment with γ-catenin, which has 86% sequence homology to β-catenin and forms an adhesion complex with β-catenin in the membrane. As a result, no RNA intramer was associated with γ-catenin in the cells, suggesting specific association of the RNA intramer with β-catenin.

Example 4

Inhibition of Transcriptional Function of β-Catenin

<4-1> Inducement of the Expression of β-Catenin

Figure 8:
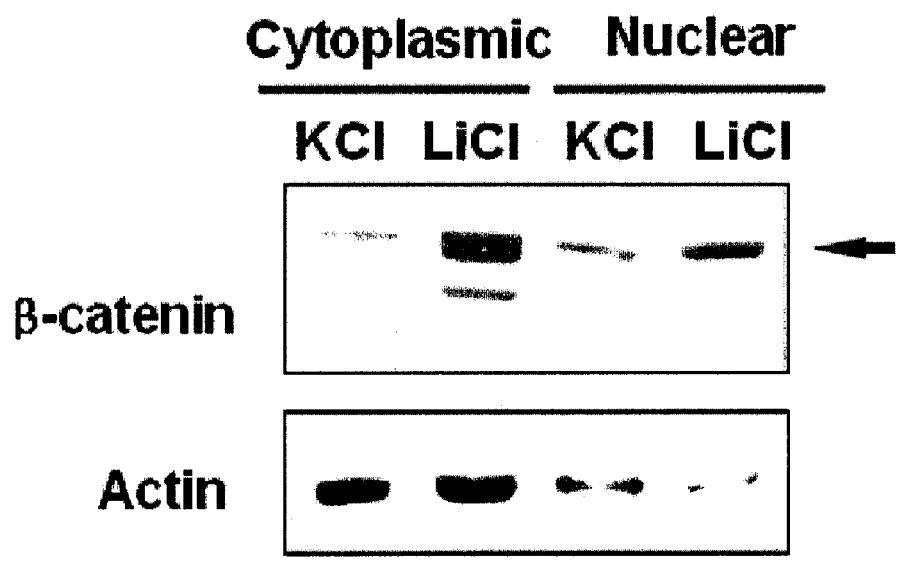
FIG. 8~FIG. 12 illustrate the regulation of target genes by U6-RNA intramer.

To see if the RNA intramer inhibited β-catenin dependent TCF transcriptional activity, lithium chloride (LiCl) was treated to 293T cells, followed by immunoblotting using anti-β-catenin antibody. As a result, the inventors confirmed that endogenous β-catenin protein was activated by the treatment of lithium chloride (FIG. 8).

Figure 9:
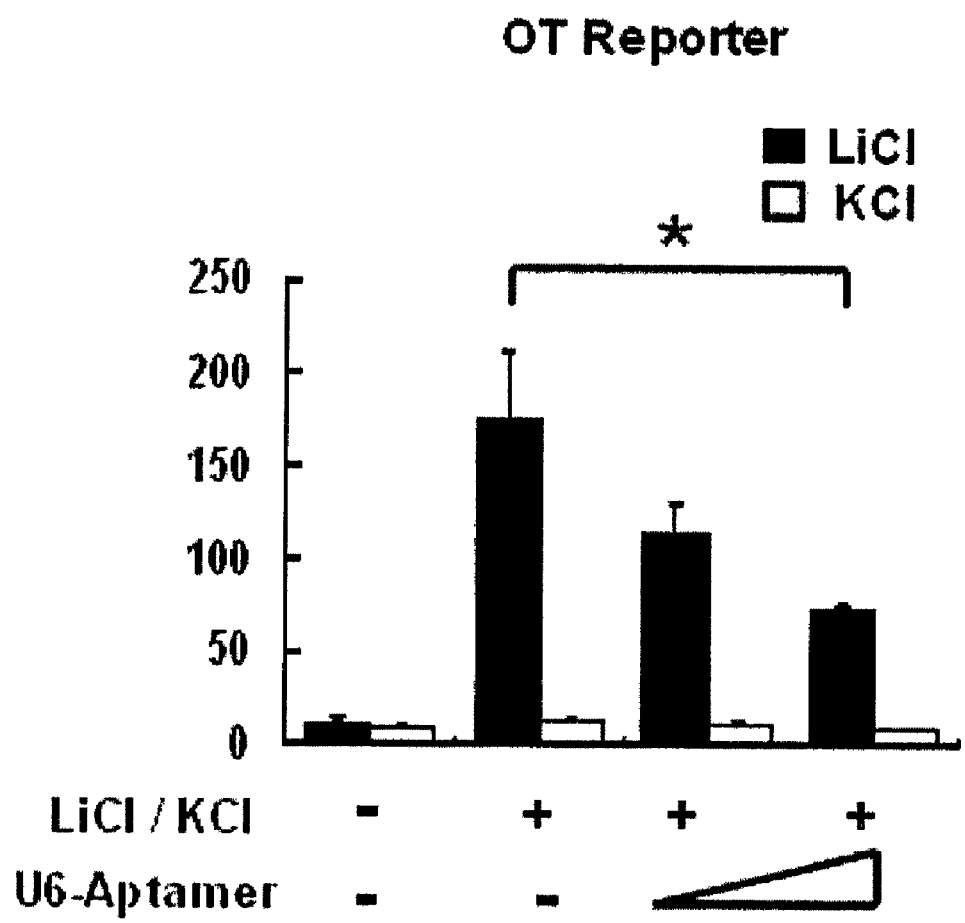
Figure 10:
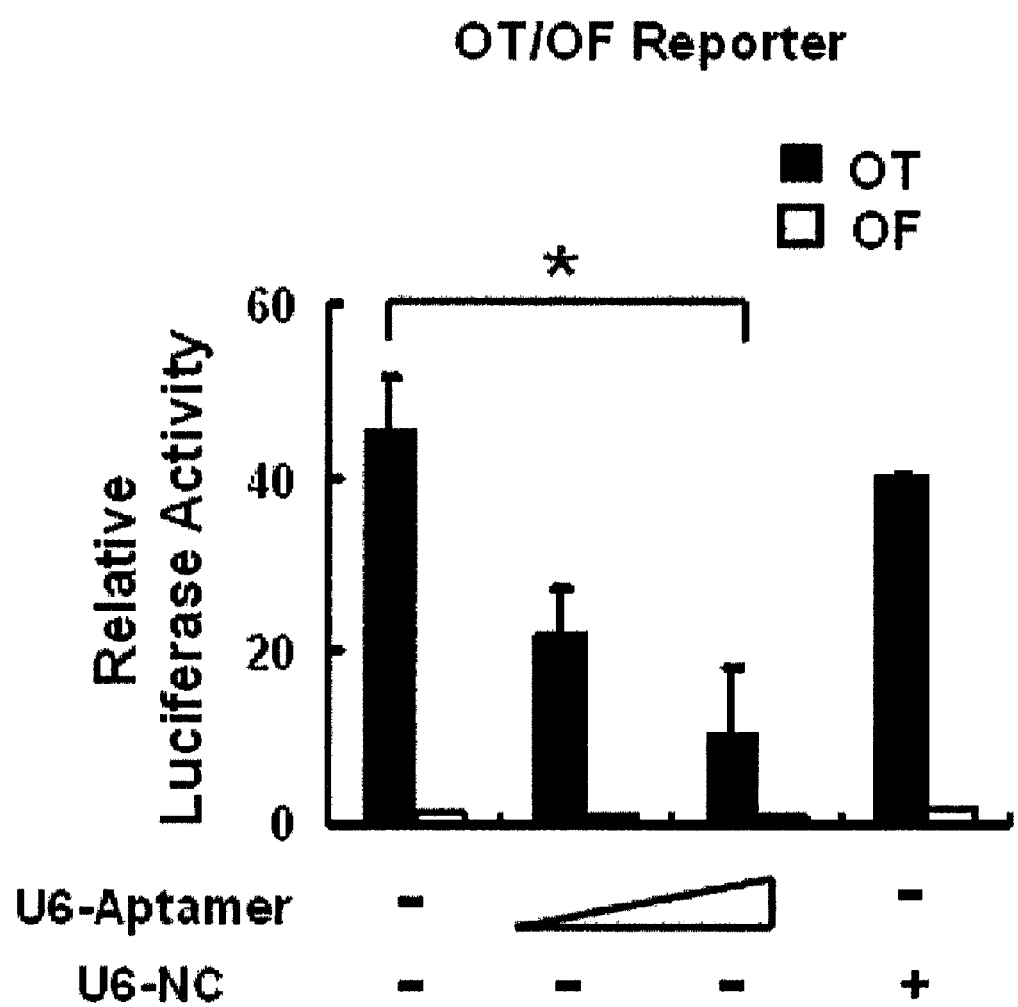

Luciferase reporters with wild type (OT) and mutant (OF) TCF binding sites were co-introduced into 293T cells with UT vector or RNA aptamer (U6-aptamer). After treating lithium chloride or calcium chloride, luciferase activity was measured. As a result, RNA intramer dose-dependent inhibition of the luciferase activity was clearly shown in the luciferase reporter with wild type (OT) TCF binding site (FIG. 9). Same experiment was performed with HCT116 colon cancer cells that express β-catenin in aberrantly high level. As a result, RNA intramer dose-dependent inhibition of luciferase activity was observed in wild-type (OT) only (FIG. 10).

The inhibitory effect was sequence-specific since the RNA intramer for the nucleocapsid protein (U6-NC) had no effect on luciferase levels.

<4-2> Inhibition of Transcriptional Function of β-Catenin
<4-2-1> RT-PCR and Northern Blot Analysis Total cellular RNA was isolated from cells with TRizol (Invitrogen), reverse transcribed with M-MuLV reverse transcriptase (Roche) and used as a template in the PCR reactions. The PCR primers represented by SEQ. ID. NO: 7 and NO: 8 were used to produce a 483 by PCR product of cyclin D1, the PCR primers represented by SEQ. ID. NO: 9 and NO: 10 were used to generate a 334 by PCR product of β-catenin and the PCR primers represented by SEQ. ID. NO: 11 and NO: 13 were used to produce a 308 by PCR product of c-myc.

For Northern blot analysis, total cellular RNA was extracted as above. RNA samples (5 μg/lane) were separated on denaturing polyacrylamide gels and blotted to nylon membranes. The blots were cross-linked with UV and hybridized with DIG-labeled RNA probes (Roche). A DIG luminescent detection kit (Roche) was used for detection.

<4-2-2> Inhibition of Transcriptional Function of β-Catenin

After confirming by luciferase assays that expression of the β-catenin was induced by lithium chloride and RNA intramer was functioning normally, the present inventors further investigated according to the method of Example <4-2-1> if the RNA intramer could inhibit the functions of β-catenin (Tetsu & McCormick, 1999; He et al., 1998) which is known to interact with the family of DNA binding TCF proteins and activate transcriptions from the cyclin D1 and c-myc promoters.

Figure 11:
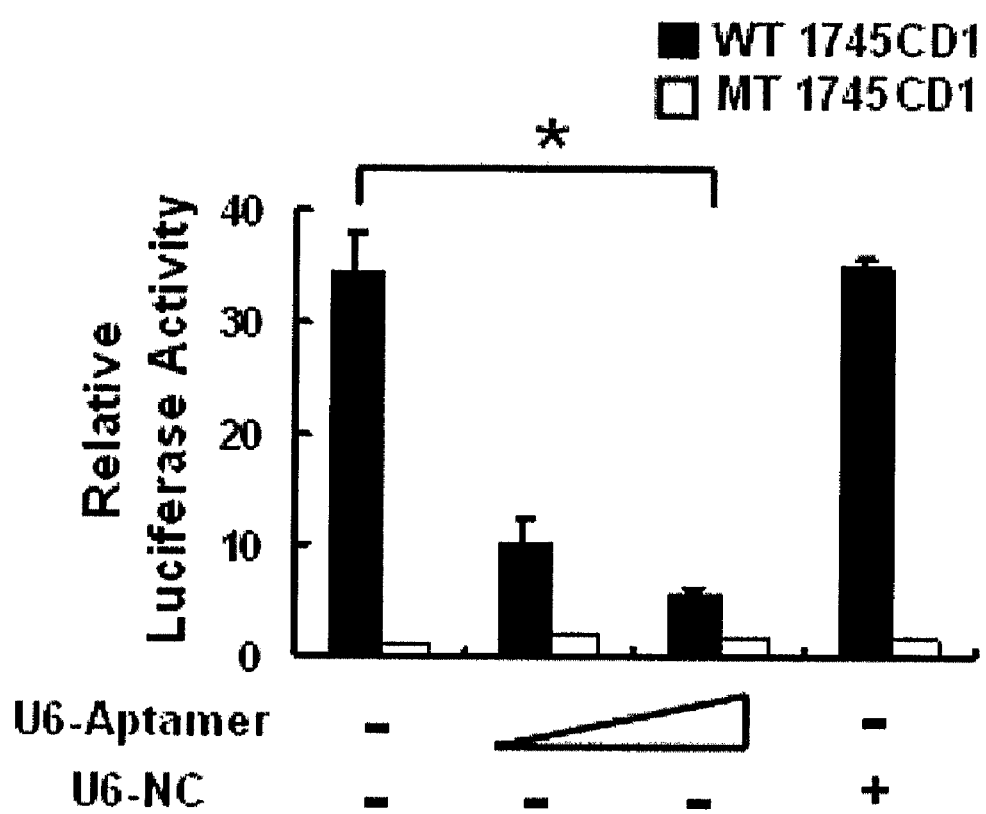
Figure 12:
Figure 12:
Figure 12:
Figure 12:
Figure 12:
Figure 12:

To see if the RNA intramer also inhibited the expression of endogenous target genes, LiCl-treated 293T cells, HCT 116 and SW480 colon cancer cell lines were transfected with the U6-RNA intramer and the expression of c-myc and cyclin D1 mRNA was measured (FIGS. 11 and 12).

As a result, expression of RNA intramer reduced expression of cyclin D1 and c-myc mRNA.

Example 5

Specific Disruption of the β-Catenin/TCF Complex

Since the U6-RNA intramer was specifically associated with nuclear β-catenin, the present inventors assumed that it might interfere with the interaction between β-catenin and TCF. The inventors first tested this notion with recombinant β-catenin and TCF proteins in vitro. Particularly, recombinant β-catenin was reacted with TCF proteins in the presence (experimental group) or absence (control group) of aptamers and the interaction between β-catenin and TCF proteins was investigated by immunoprecipitation using anti-β-catenin antibody and Western blotting.

Figure 13:
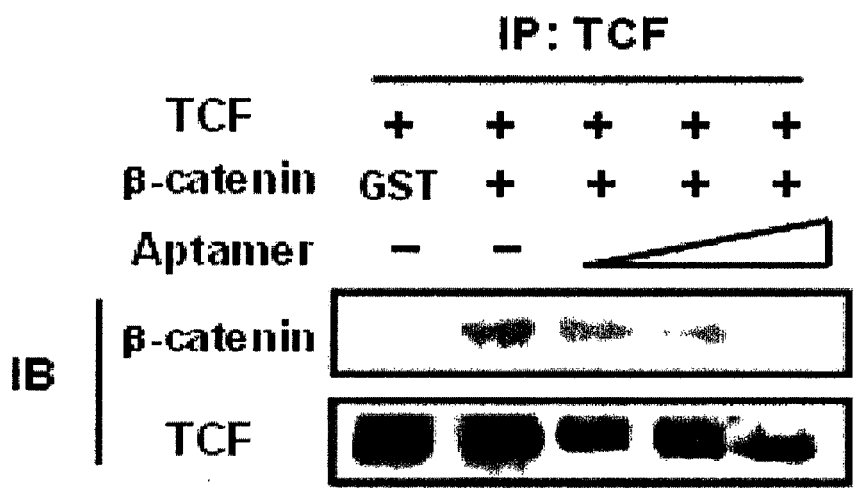
FIG. 13 and FIG. 14 illustrate the results of co-immunoprecipitation assay of cells expressing pDHFR-aptamer.

As a result, binding between β-catenin and TCF proteins was inhibited by the U6-RNA intramer, suggesting that the high affinity RNA aptamer competed with TCF for β-catenin (FIG. 13).

Figure 14:
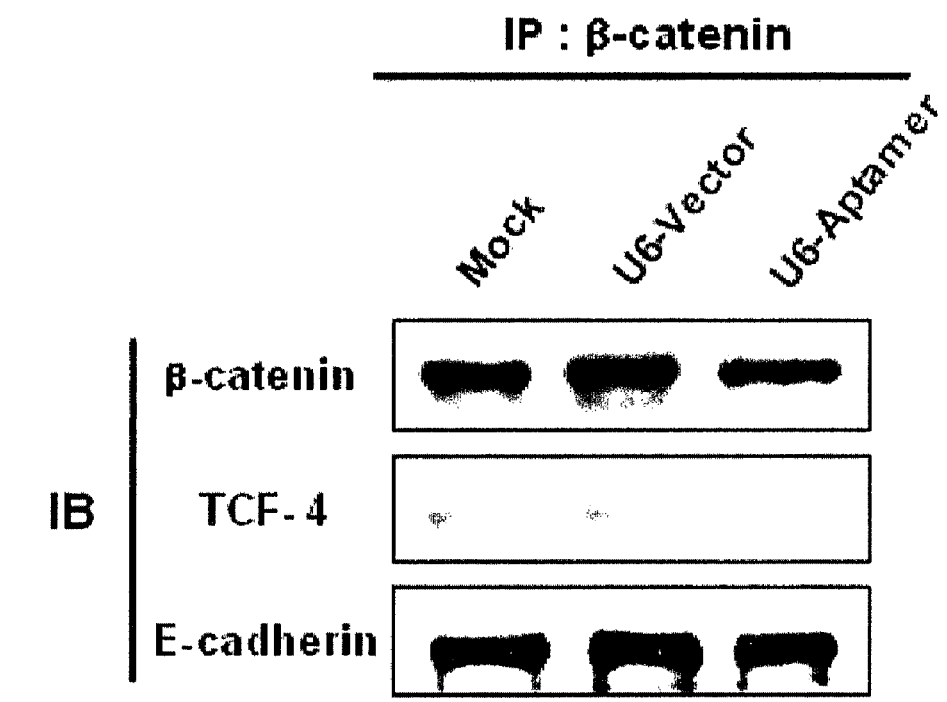

The present inventors next tested whether the formation of nuclear protein complexes was inhibited by the RNA aptamer (FIG. 14). Co-immunoprecipitation assay showed that the β-catenin/TCF-4 interaction was disrupted by the RNA intramer, but that between β-catenin and E-cadherin was not.

As a control, the present inventors also constructed β-catenin binding RNA intramer as a fusion transcript with aberrantly spliced DHFR transcript (Kim & Jeong, Biochem. Biophys. Res. Commun 320:1181-1186, 2004) and tested its effect on the protein-protein interactions (FIGS. 13 and 14). DHFR-intramer inhibited β-catenin protein interaction with TCF-4 as well as that with E-cadherin, because of its ubiquitous over-expression in mammalian cells (Kim & Jeong, Biochem. Biophys. Res. Commun 320:1181-1186, 2004). This indicates that the U6-RNA intramer specifically disrupts the nuclear transcription complex, not the cytoplasmic cell adhesion complex, probably because expression of the U6-RNA intramer is restricted to the nucleus.

Example 6

Inhibition of Tumorigenesis by the RNA Aptamer

<6-1> Selection of Stable Aptamer Transfectants

Since the RNA intramer reduced the expression of β-catenin target genes in transient transfection experiments, the present inventors were interested in examining its effect in the cell lines that stably express RNA.

Figure 15:
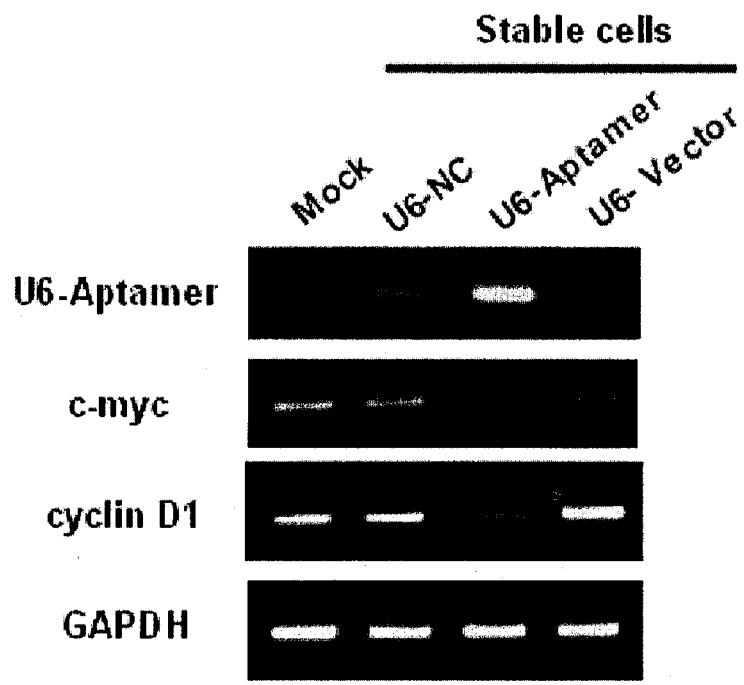
FIG. 15~FIG. 18 illustrate the results of immunofluorscent assay of the stable cell lines expressing the RNA intramer.
Figure 16:
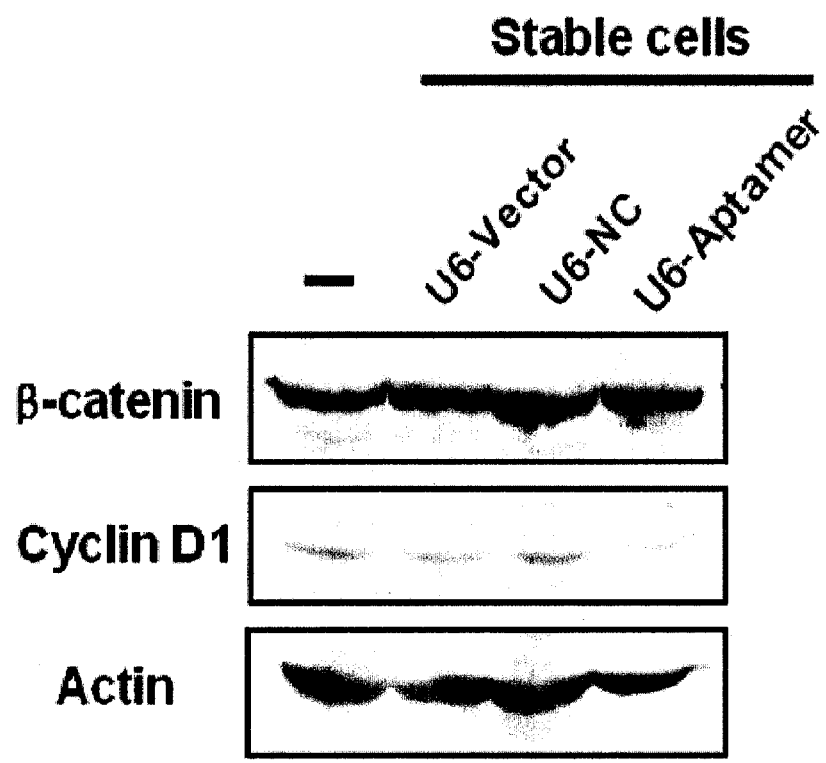

HCT116 cells were co-transfected with pU6-aptamer, pU6-NC, or pU6-vector in the presence of pTK-Hyg (Clontech). Stably transfected clones were selected with hygromycin B (Invitrogen). After 2 weeks, hygromycin resistant clones were tested for expression of the RNA aptamer by RT-PCR. The expressions of cyclin D1 and c-myc were also measured by RT-PCR. As a result, as shown in FIG. 15 and FIG. 16, levels of mRNA (cyclin D1 and c-myc) and cyclin D1 protein were reduced, compared with the parental strain. The morphology of the stable aptamer HCT 116 cell line did not differ from the stable cell lines carrying U6-RNA (vector) or the nucleocapsid(NC)-binding RNA intramer (FIGS. 15-18).

<6-2> Investigation of Cell Cycle and Soft Agar Colony Formation

Since the cyclin D1 expression was low in the stable RNA intramer cell line, it seemed likely that these cell lines would tend to be arrested in the G1/S transition of the cell cycle. Therefore, the present inventors performed the flow cytometric analysis to confirm the notion.

For the flow cytometric analysis, HCT116 cell lines (10,000 cells/sample) stably expressing aptamers were trypsinized and fixed in 70% ethanol. They were then stained with propidium iodide (10 μg/ml) and incubated for 30 minutes at 37° C. Cell cycle profiles were analyzed on a FACScaliber with Celiquest Software (Becton Dickinson).

Figure 17:
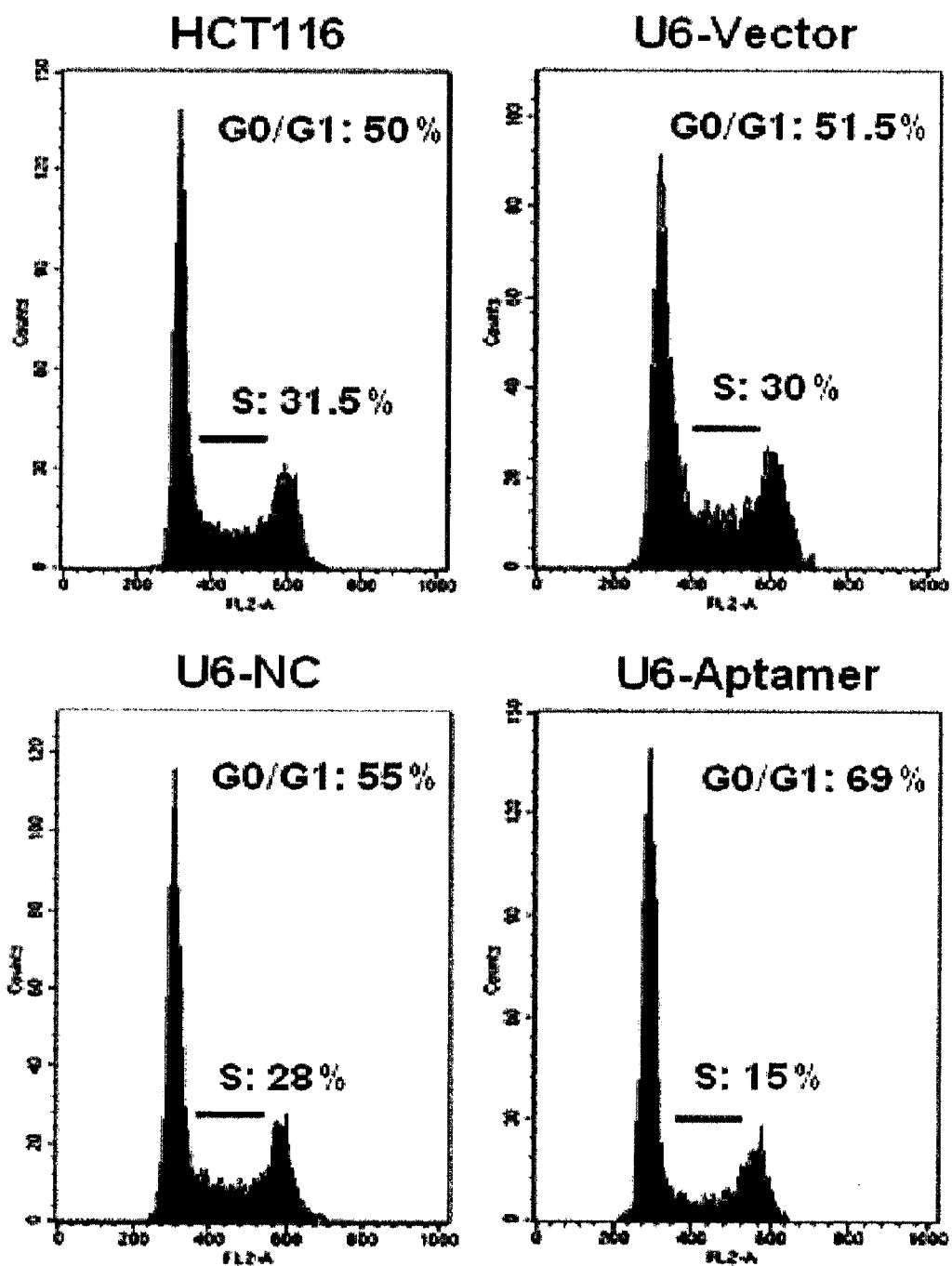

As a result, a significant proportion of the cells of cell line #6 was arrested in G1 (FIG. 17).

Figure 18:
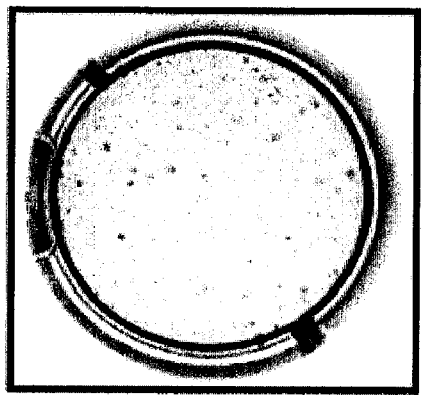
Figure 18:
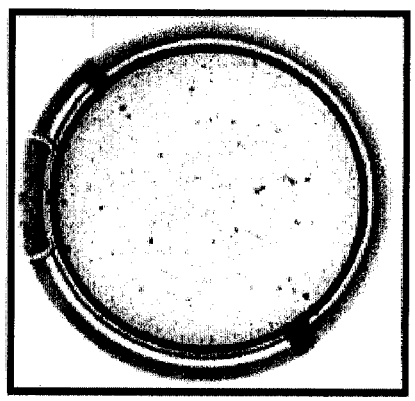
Figure 18:
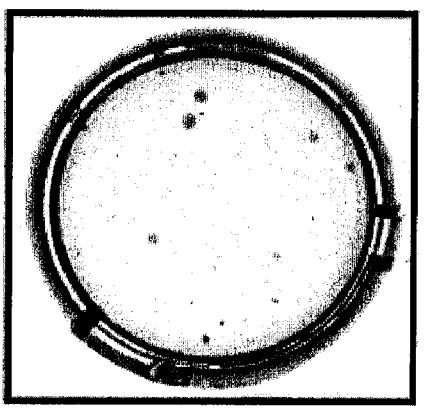
Figure 18:
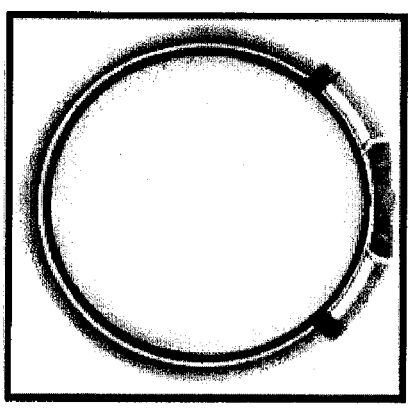
Figure 19:
FIG. 19 and FIG. 20 illustrate the bindings of RNA aptamer #10 to DNA binding domains of TCF-1 proteins.
Figure 19:
Figure 19:

The present inventors performed soft agar colony formation assay to test if the cell line could reduce tumorigenesis. 5000 cells were seeded in six well plates with 0.7% agar. After 10 days, colonies formed were fixed in 70% ethanol, washed with water and stained with 0.005% crystal violet for 20 minutes. No colonies were formed by the RNA intramer #6 stable cell line, whereas the control stable cell lines formed large number of colonies (FIG. 18). These observations strongly suggest that the β-catenin-binding RNA intramer is effective in arresting cell division and ultimately reducing tumorigenesis.

TCF-1 Binding Aptamer

Example 7

Plasmid Proteins and Reagents

The present inventors inserted the authentic mouse TCF-1 encoding region into EcoRI site of pcDNA3.1 vector (S. Jeong et al., Kor. J. Biol. Sci. 4:389-394, 2000). PCR was performed with primers containing EcoRI (5' primer, N100 and full length TCF-1: SEQ. ID. NO: 16, C200: SEQ. ID. NO: 19) and Sal I (3' primer, N100: SEQ. ID. NO: 17, full length TCF-1 and C200: SEQ. ID. NO: 20) restriction enzyme sites, using DNA polymerase (Taq polymerase, Takara) as follows; predenaturation at 94° C. for 5 minutes, denaturation at 94° C. for 1 minute, annealing at 55° C. for 1 minute, polymerization at 72° C. for 1 minute, 30 cycles from denaturation to polymerization, and final extension at 72° C. for 10 minutes. The PCR products (C200: amino acid 188-388, N100: amino acid 5-100, full length TCF-1 protein: amino acid 5-388) were cut by EcoR I and Sal I, cloned with pGEX 4T-1 plasmid to construct an expression vector for the recombinant TCF-1 protein. Each recombinant protein was expressed by the expression vector above and thus GST-TFP-1 protein and $(His)_6$-NFAT-1 were purified as described above (S. Y. Lee and S. Jeong, Mol. Cell. 17: 174-179, 2004; M. Y. Kim and S. Jeong, Biochem. Biophys. Res. Commun. 320: 1181-1186, 2004).

Example 8

Specific Bond Between RNA Aptamer #10 and TCF-1 Protein DNA Binding Domain

RNA aptamer #10 represented by SEQ. ID. NO: 13 was radio-labeled ($\alpha$-$^{32}$P UTP) and incubated with GST-fused TCF-1 protein, followed by GST pull-down assay. RNA-protein complex was precipitated with glutathione-sepharose (GST) 4B beads and bound RNA aptamers were eluted in 5 mM EDTA. Electrophoresis was performed on 6% polyacrylamide/7 M urea gel, followed by autoradiography.

Figure 20:
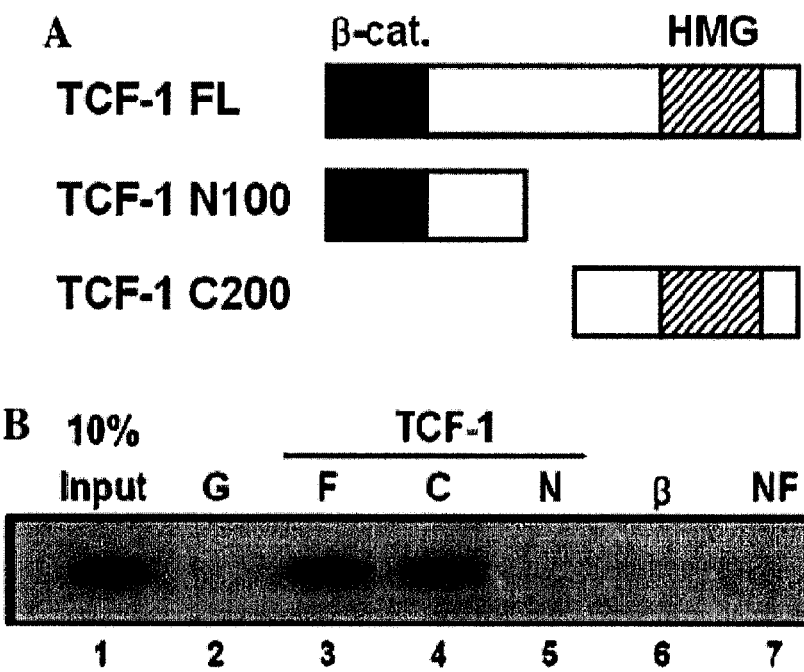
Figure 21:
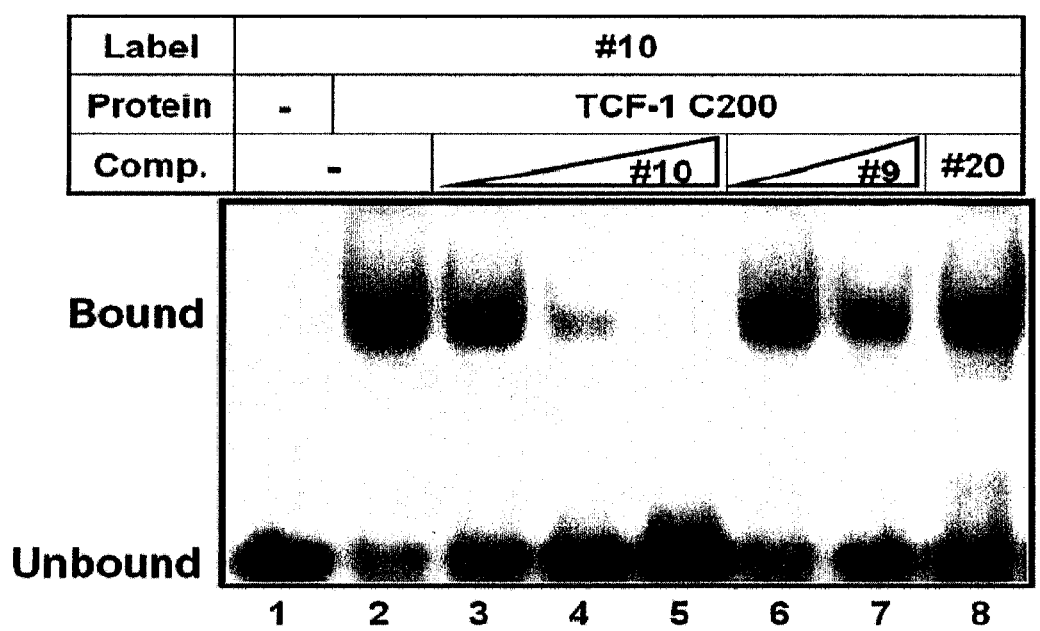
FIG. 21 and FIG. 22 illustrate the binding specificity of RNA aptamer #10 to TCF-1 protein.
Figure 22:
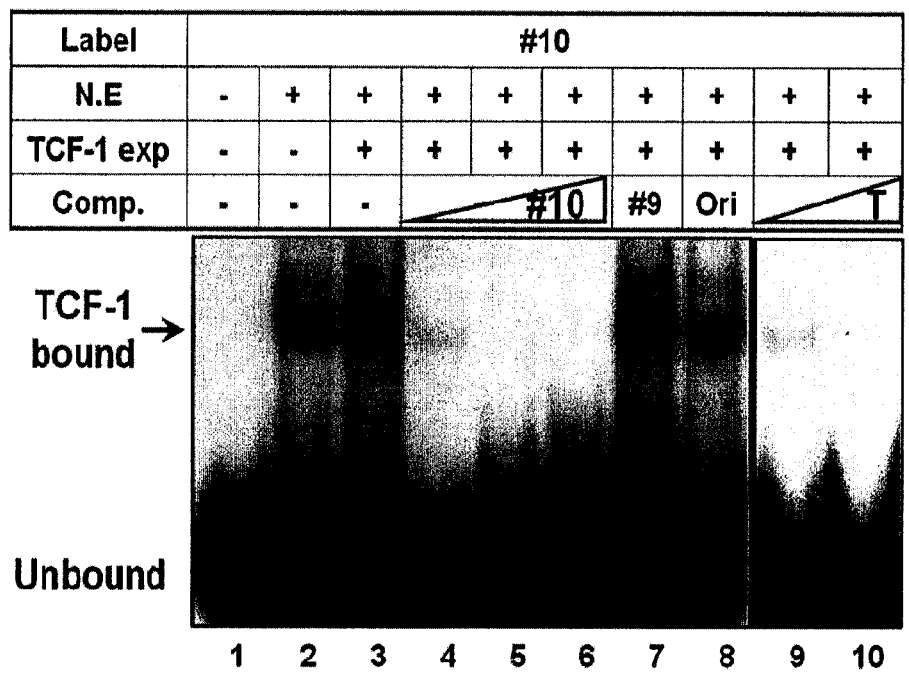

As a result, as shown in FIG. 20, RNA aptamer #10 bound to DNA binding site containing HMG domain (C200, C) but did not bind to N-terminal β-catenin binding domain (N100, N) or to other DNA binding domains of such proteins as β-catenin or NFAT (NF). The results suggest that the RNA aptamer #10 of the present invention specifically binds to HMG domain of TCF-1.

Example 9

Competition of the RNA Aptamer #10 and Non-Specific RNA

<9-1> Preparation of Nuclear Extracts

Human embryonic kidney 293T cells and murine immature thymoma cell line S49.1 (American Type Culture Collection) were cultured in Dulbecco's modified Eagle's medium with 10% fetal bovine serum and antibiotics. The human embryonic kidney 293T cells were transfected with GST-TCF-1 vector. The S49.1 cell line has characteristics of CD4/CD8 double negative immature thymocytes, has a high level of TCF-1, and may be regulated by TCF signaling (S. H. Jeon et al., J. Exp. Med. 185: 1827-1836, 1997). 293T cells ($1 \times 10^7$ cells) and S49.1 cells ($1 \times 10^8$ cells) were harvested and washed twice with ice-cold PBS. Cell pellets were resuspended in 200 μl ice-cold buffer A (20 mM Tris-Cl (pH 8.0), 10 mM NaCl, 1 mM EDTA, 1 mM DTT, 1 mM PMSF, protease inhibitor cocktail, phosphatase inhibitor cocktail) supplemented with the protease inhibitor cocktail and the phosphatase inhibitor cocktail (Sigma-Aldrich). After incubating for 15 minutes on ice, cells were lysed with 0.5% NP-40 and gently vortexed. Cell lysates were centrifuged at 4000 rpm at 4° C. for 30 minutes. Pellets were resuspended in 50 ml ice-cold buffer C (20 mM Tris-Cl (pH8.0), 400 mM NaCl, 1.5 mM $MgCl_2$, 0.2 mM EDTA, 0.5 mM PMSF, 25% glycerol, protease inhibitor cocktail, phosphatase inhibitor cocktail). After incubating for 30 minutes on ice, debris was pelleted by centrifugation and the supernatant was obtained. Protein concentrations in the cleared nuclear extracts were measured by the Bradford assay (Bio-Rad).

<9-2> Electrophoretic Mobility Shift Assay (EMSA)

To test TCF-1 protein specific binding affinity of the RNA aptamer #10, the present inventors made the RNA aptamer #10 to compete other RNAs for binding to TCF-1 protein.

Nuclear extracts (5.25 μg of S49.1) were incubated with radiolabeled RNA aptamer #10, non-radiolabeled RNA aptamer #10, non-specific RNA aptamers #9 (SEQ. ID. NO: 14) and #20 (SEQ. ID. NO: 15) at room temperature for 30 minutes in the presence of 0.2 μg poly (dI-dC). DNA-protein complexes were separated on a 5% native polyacrylamide gel in 1×TBE at 150 V for 4 hours and visualized by autoradiography.

As a result, the increase of non-labeled RNA (#10, #9, #20) reduced the intensity of the bound band, which is TCF-1 binding radiolabeled RNA aptamer #10. However, the bound band was not weaker by TCF-1 non-binding RNA #9 or original RNA pool (Ori). Therefore, it was confirmed that non-binding RNA molecule (#9, #20) did not compete with RNA aptamer #10 for binding to TCF-1.

Example 10

Inhibition of DNA Binding to TCF-1 by RNA Aptamer #10

The present inventors performed EMSA (electrophoretic mobility shift assay) with DNA oligonucleotide (TRE, TCF responsive element, SEQ. ID. NO: 21) containing TCF-1 binding domain (A/T A/T CAAAG).

<10-1> Preparation of TRE Oligonucleotide

Double-stranded TRE oligonucleotide represented by SEQ. ID. NO: 12 was synthesized by Bioneer. The DNA was end-labeled with 20 U of T4 polynucleotide kinase and 50 μCi[γ-$^{32}$P]ATP, and purified on a G-50 Sephadex spin column (Sigma), followed by phenol extraction and ethanol precipitation.

<10-2> EMSA

TRE oligonucleotide prepared in Example <10-1> was added to the nuclear extracts (5.25 μg of S49.1) and incubated with unlabeled RNA aptamer #10 and tRNA in the presence of 0.2 μg poly (di-dC) (Roche), followed by EMSA as described above in Example <9-2>.

Figure 23:
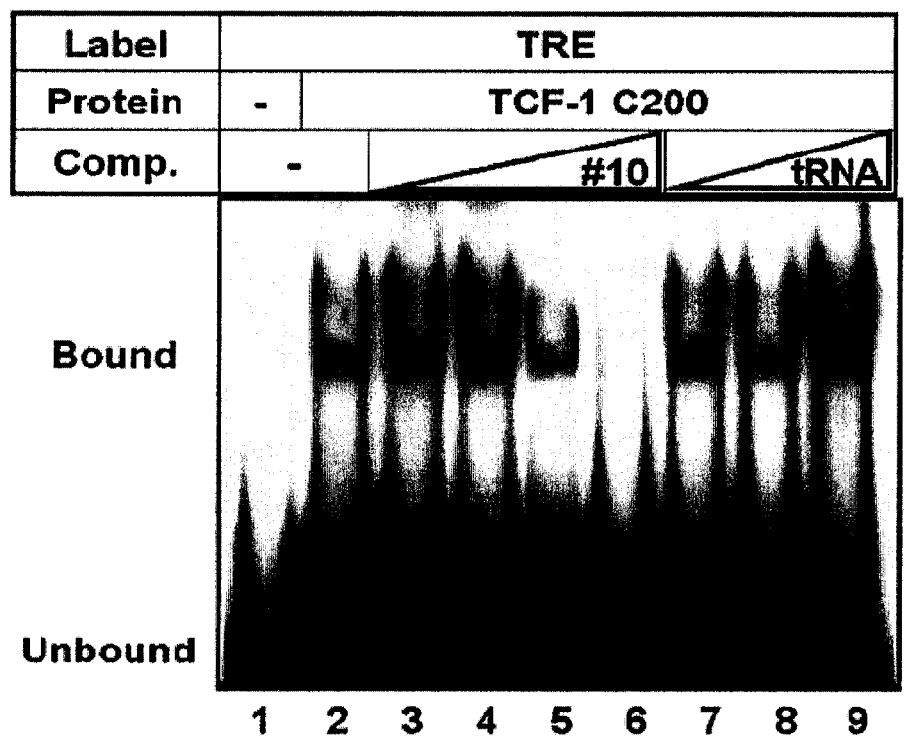
FIG. 23 and FIG. 24 illustrate the DNA binding inhibition of RNA aptamer #10 to TCF-1.

As a result, binding of TRE to TCF-1 C200 protein was gradually competed by increasing concentration of unlabeled RNA aptamer #10, but not by non-specific tRNA (FIG. 23).

The present inventors also observed the specific inhibition of TRE binding to TCF-1 full-length protein by RNA aptamer #10.

As a result, TRE binding to TCF-1 full-length protein was inhibited by RNA aptamer #10, but other RNAs, such as HIV-1 nucleocapsid (NC) protein binding RNA aptamer (M.

Figure 24:
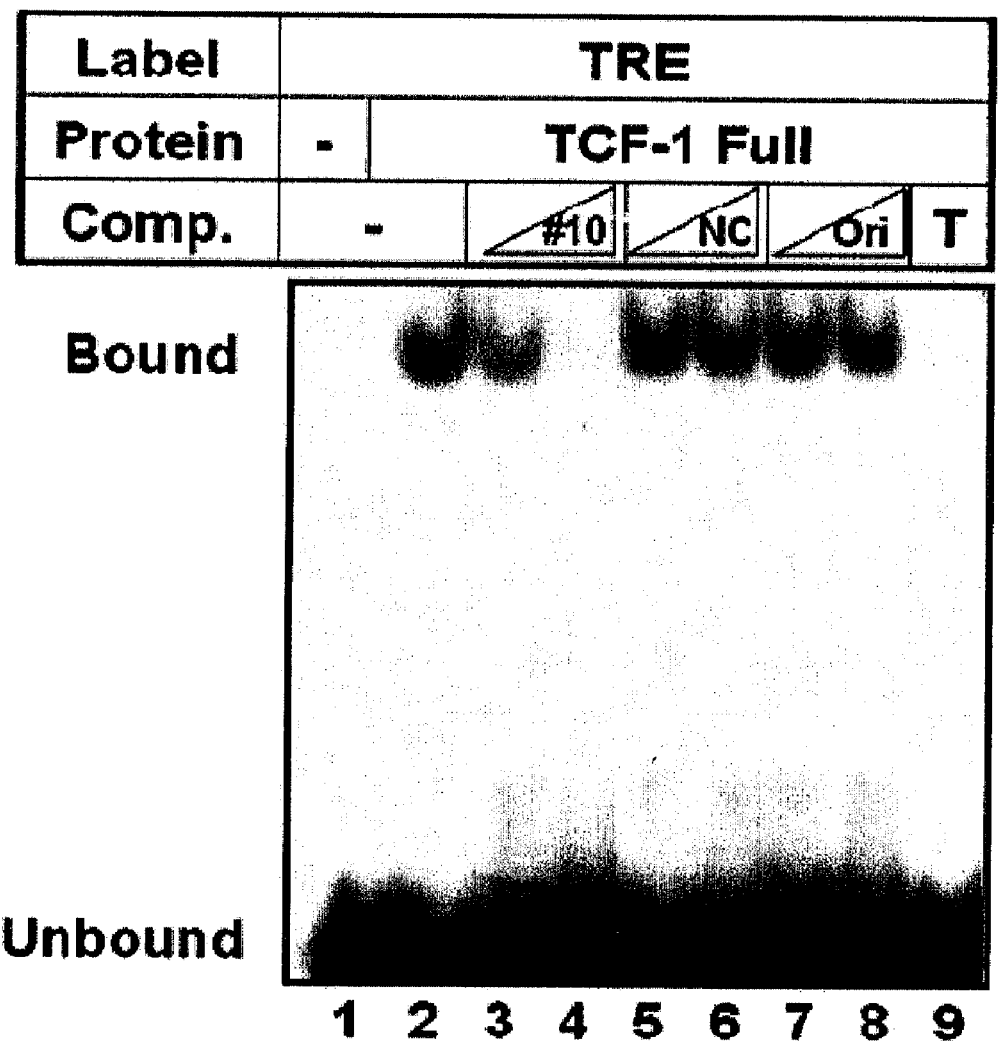
Figure 25:
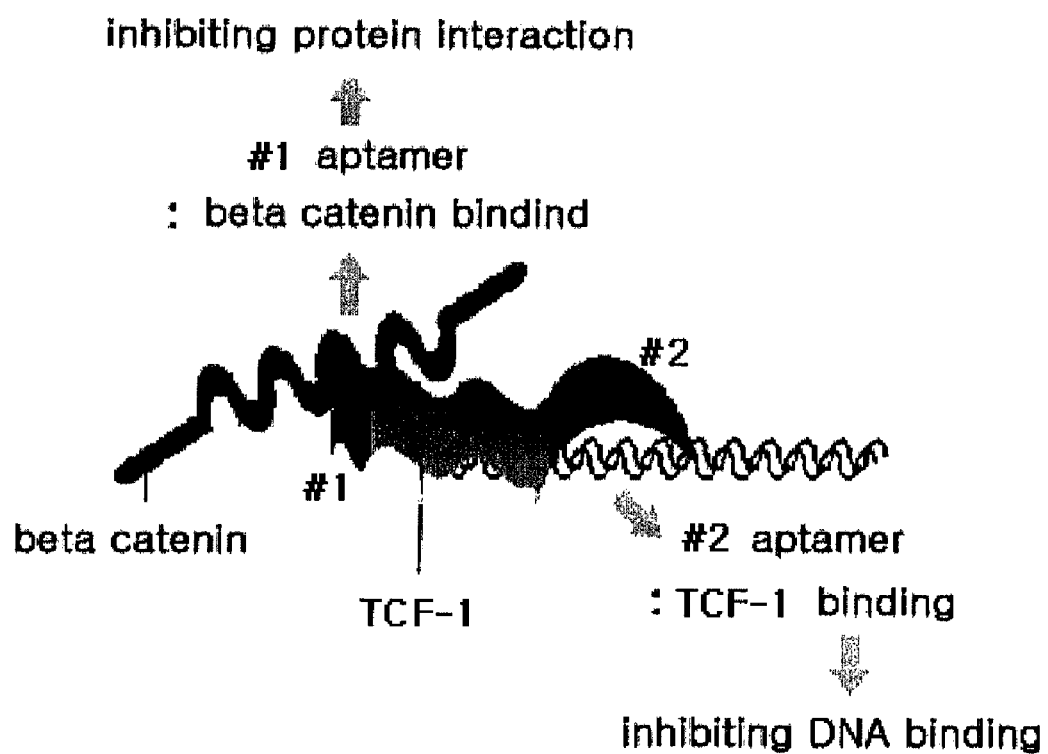
FIG. 25 is a schematic diagram illustrating the binding site of the β-catenin binding aptamer to TCF-1 binding aptamer.

Y. Kim and S. Jeong, Biochem. Biophys. Res. Commun. 320: 1181-1186, 2004) or original RNA library, did not compete for the binding (FIG. 24).

The above results indicate that RNA aptamer #10 inhibits DNA binding to TCF-1 both in vivo and in vitro.

Manufacturing Example

Preparation of Injectable Solutions

The present inventors prepared injectable solutions containing 100 nM of the RNA aptamer of the invention as an effective ingredient as follows.

1 g of 5'-chloro-3,2'-dihydroxychalcone or 5'-chloro-2,3'-dihydroxychalcone.hydrochloride, 0.6 g of sodium chloride and 0.1 g of ascorbic acid were dissolved in distilled water to make 100 me of solution. The solution was put in a bottle and heated at 20° C. for 30 minutes for sterilization.

The constituents of the injectable solutions are as follows.
RNA aptamer—5 μg (100 nM)
5'-chloro-3,2'-dihydroxychalcone or 5'-chloro-2,3'-dihydroxychalcone.hydrochloride—1 g
Sodium chloride—0.6 g
Ascorbic acid—0.1 g
Distilled water—Proper amount

INDUSTRIAL APPLICABILITY

As explained hereinbefore, the RNA aptamer binding to the β-catenin inhibits the transcription activity of β-catenin and reduces the expressions of target genes, so that it can be effectively used as an anticancer agent that acts as a β-catenin/TCF transcription complex inhibitor, pathologic protein-protein interaction specific inhibitor and β-catenin, known as an oncogene, inhibitor. By binding itself to DNA binding domain of TCF-1, RNA aptamer can inhibit the binding of TCF-1 to a target gene, leading to the interference of the expression of the target gene. Thus, it can be useful for explaining the functions of TCF-1 protein as well. Considering that most target genes are cancer-related genes such as cyclin D or c-myc, RNA aptamer that disrupts the DNA binding of TCF-1 can be effectively used for the development of an anticancer agent and the screening of anticancer agent candidates.

Sequence List Text

SEQ. ID. NO: 1 is the RNA aptamer sequence binding to β-catenin,
SEQ. ID. NO: 2 is the RNA intramer sequence binding to β-catenin,
SEQ. ID. NO: 3 and NO: 4 are primer sequences for amplifying β-catenin (Arm 1-12, amino acids 129-695),
SEQ. ID. NO: 5 and NO: 6 are primer sequences for amplifying the aptamer region from pUC19-aptamer,
SEQ. ID. NO: 7 and NO: 8 are primer sequences for amplifying 483 by region of cyclin D1,
SEQ. ID. NO: 9 and NO: 10 are primer sequences for amplifying 334 by region of β-catenin,
SEQ. ID. NO: 11 and NO: 12 are primer sequences for amplifying 308 by region of c-myc,
SEQ. ID. NO: 13 is the sequence of RNA aptamer #10,
SEQ. ID. NO: 14 is the sequence of non-specific RNA aptamer #9,
SEQ. ID. NO: 15 is the sequence of non-specific RNA aptamer #20,
SEQ. ID. NO: 16 is the sequence of 5' primer, N100 and full length TCF-1,
SEQ. ID. NO: 17 is the sequence of 3' primer, N100,
SEQ. ID. NO: 18 is the sequence of full-length TCF-1 primer,
SEQ. ID. NO: 19 is the sequence of C200,
SEQ. ID. NO: 20 is the sequence of full-length TCF-1 and C200,
SEQ. ID. NO: 21 is the sequence of TRE (TCF responsive element),
SEQ. ID. NO: 22 and NO: 23 are the sequence of GAPDH primer, Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A RNA aptamer consisting of SEQ ID NO: 1 and having the functional characteristic of being capable of specifically binding to β-catenin.

2. A gene expression regulator containing the RNA aptamer of claim 1.

3. The gene expression regulator according to claim 2, wherein the gene is a cyclin D1 gene or a c-myc gene.

4. An inhibitor of the interaction between β-catenin and other proteins, containing the RNA aptamer of claim 1.

5. A recombinant vector that expresses β-catenin binding RNA intramer, wherein the RNA intramer is encoded by SEQ ID NO: 2.

6. An anticancer agent containing a recombinant vector that expresses the RNA aptamer of claim 1 as an effective ingredient.

7. An anticancer agent containing the recombinant vector of claim 5 as an effective ingredient.

* * * * *